US011613571B2

(12) United States Patent
Akinseye et al.

(10) Patent No.: US 11,613,571 B2
(45) Date of Patent: Mar. 28, 2023

(54) BIOPHARMACEUTICAL COMPOSITIONS COMPRISING ANTIBODY VARIANTS

(71) Applicant: GLAXOSMITHKLINE INTELLECTUAL PROPERTY DEVELOPMENT LIMITED, Brentford (GB)

(72) Inventors: Chika Akinseye, Stevenage (GB); Tejinder Bhinder, Stevenage (GB); Li Cui, Collegeville, PA (US); Steven Grant, Stevenage (GB); Laura Hook, Stevenage (GB); Alan Peter Lewis, Stevenage (GB); Martin Anibal Orecchia, Stevenage (GB)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 66 days.

(21) Appl. No.: 17/056,816

(22) PCT Filed: May 21, 2019

(86) PCT No.: PCT/IB2019/054198
§ 371 (c)(1),
(2) Date: Nov. 19, 2020

(87) PCT Pub. No.: WO2019/224724
PCT Pub. Date: Nov. 28, 2019

(65) Prior Publication Data
US 2021/0115128 A1   Apr. 22, 2021

Related U.S. Application Data

(60) Provisional application No. 62/828,515, filed on Apr. 3, 2019, provisional application No. 62/675,936, filed on May 24, 2018, provisional application No. 62/675,291, filed on May 23, 2018.

(51) Int. Cl.
C07K 16/24    (2006.01)

(52) U.S. Cl.
CPC ........ *C07K 16/244* (2013.01); *C07K 2317/51* (2013.01); *C07K 2317/515* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 2015/0196663 A1* | 7/2015 | Shusta | .............. | A61K 9/0085 435/254.11 |
| 2015/0266947 A1* | 9/2015 | Sierks | .................. | A61P 25/28 435/6.12 |
| 2017/0355756 A1* | 12/2017 | Julien | ................... | A61P 9/10 |

FOREIGN PATENT DOCUMENTS

| | | | |
|---|---|---|---|
| WO | WO 2008068048 | * | 6/2008 |
| WO | WO 2017/033121 A1 | | 3/2017 |
| WO | WO 2018/215964 A1 | | 11/2018 |

OTHER PUBLICATIONS

Cheng "In vitro and in vivo modifications of recombinant and human IgG antibodies" mabs 6(5):1145-1154 (Year: 2014).*
Kussie "A Single Engineered Amino Acid Substitution Changes Antibody Fine Specificity" J immunol 152(1): 146-52 (Year: 1994).*
Chen "Enhancement and destruction of antibody function by somatic mutation: unequal occurrence is controlled by V gene combinatorial associations" EMBO 14(12):2784-2794 (Year: 1995).*
Khetan et al., "Control of misincorporation of serine for asparagine during antibody production using CHO cells", *Biotechnology and Bioengineering*, vol. 107, No. 1, pp. 116-123 (2010).
Liddament et al., "P155 Higher binding affinity and in-vitro potency of reslizumab for interleukin-5 compared with mepolizumab", *Annals of Allergy, Asthma & Immunology*, vol. 117, No. 5, 1 page (2016).
Liu et al., "In vitro and in vivo modifications of recombinant and human IgG antibodies", *mAbs, Landes Bioscience*, US, vol. 6, No. 5, pp. 1145-1154 (2014).

* cited by examiner

*Primary Examiner* — Adam Weidner
(74) *Attorney, Agent, or Firm* — Cynthia Lan Martin; Duke Fitch

(57) ABSTRACT

The present disclosure relates to compositions comprising antibody variants, for treating interleukin 5 (IL-5) mediated diseases, and related methods.

19 Claims, No Drawings
Specification includes a Sequence Listing.

BIOPHARMACEUTICAL COMPOSITIONS COMPRISING ANTIBODY VARIANTS

This application is a 371 of International Application No. PCT/IB2019/054198 filed 21 May 2019, which claims the benefit of U.S. Provisional Application No. 62/675,291 filed 23 May 2018, U.S. Provisional Application No. 62/675,936 filed 24 May 2018 and U.S. Provisional Application No. 62/828,515 filed 03 Apr. 2019, the disclosures of which are incorporated herein in their entireties.

FIELD OF THE DISCLOSURE

The present disclosure relates to compositions comprising antibody variants, for treating interleukin 5 (IL-5) mediated diseases.

BACKGROUND OF THE DISCLOSURE

IL-5 is a secreted protein. IL-5 plays a role in a number of different diseases such as asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis. These serious diseases affect hundreds of millions of people world wide.

This means a need exists for compositions suitable for treating IL-5 mediated disease. Such compositions are provided by the present disclosure.

SUMMARY OF THE DISCLOSURE

One aspect of the disclosure is a composition comprising a) a first antibody having a heavy chain amino acid sequence as shown in SEQ ID NO: 1 and a light chain amino acid sequence shown in SEQ ID NO: 2; and b) a first variant form of the first antibody comprising at least one serine residue at a position selected from the group consisting of position 60 of SEQ ID NO: 1, position 317 of SEQ ID NO: 1 and position 363 of SEQ ID NO: 1.

Another aspect of the disclosure is a composition comprising a) a first antibody having a heavy chain amino acid sequence as shown in SEQ ID NO: 1 and a light chain amino acid sequence shown in SEQ ID NO: 2; and b) a second variant form of the first antibody comprising at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; and b) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a first variant form of the first antibody comprising at least one serine residue at a position selected from the group consisting of position 60 of SEQ ID NO: 1, position 317 of SEQ ID NO: 1 and position 363 of SEQ ID NO: 1; and c) a second variant form of the first antibody comprising at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a first variant form of the first antibody comprising at least one serine residue at a position selected from the group consisting of position 60 of SEQ ID NO: 1, position 317 of SEQ ID NO: 1 and position 363 of SEQ ID NO: 1; and c) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a second variant form of the first antibody comprising at least one serine residue at a position selected from the group consisting of position 22 of SEQ ID NO: 2, position 37 of SEQ ID NO: 2 and position 216 of SEQ ID NO: 2; and c) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a first variant form of the first antibody comprising at least one serine residue at a position selected from the group consisting of position 60 of SEQ ID NO: 1, position 317 of SEQ ID NO: 1 and position 363 of SEQ ID NO: 1; c) a second variant form of the first antibody comprising at least one serine residue at a position selected from the group consisting of position 22 of SEQ ID NO: 2, position 37 of SEQ ID NO: 2 and position 216 of SEQ ID NO: 2; and d) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

DETAILED DESCRIPTION OF THE DISCLOSURE present disclosure provides compositions for treating interleukin 5 (IL-5) mediated diseases, and related subject matter. The compositions of the disclosure comprise the 28Y042-7F11-1 antibody and variants of this antibody. The 28Y042-7F11-1 antibody binds human IL-5 and antagonizes its activity. Compositions comprising the 28Y042-7F11-1 antibody are useful for decreasing the absolute blood eosinophil count in a subject and may be used to treat conditions where this is desirable. This means the compositions of the disclosure comprising the 28Y042-7F11-1 antibody and variants of this antibody are useful for treating a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis.

28Y042-7F11-1 is a monoclonal antibody comprising the heavy chain amino acid sequence shown in SEQ ID NO: 1 and the light chain amino acid sequence shown in SEQ ID NO: 2. 28Y042-7F11-1 comprises the heavy chain amino acid sequence shown in SEQ ID NO: 1 and the light chain amino acid sequence shown in SEQ ID NO: 2. The 28Y042-7F11-1 antibody binds human IL-5 and antagonizes its activity. 28Y042-7F11-1 is a recombinant humanized monoclonal antibody (IgG$_1$, Kappa). 28Y042-7F11-1 has two light and two heavy chains. The 28Y042-7F11-1 heavy chain is encoded by the nucleic acid sequence shown in SEQ ID NO: 15. The 28Y042-7F11-1 light chain is encoded by the nucleic acid sequence shown in SEQ ID NO: 16. The 28Y042-7F11-1 heavy and light chains are covalently linked by a single disulfide bond and the heavy chains are linked to each other by two disulfide bonds resulting in a typical IgG molecule.

The term "antigen binding protein", as used herein refers to isolated antibodies, antibody fragments (e.g., Fabs etc.) and other antibody derived protein constructs—such as those comprising antibody domains (e.g., domain antibodies etc.)—which are capable of binding to human IL-5 (SEQ ID NO: 11).

The term "antibody" as used herein refers to molecules with an immunoglobulin-like domain (e.g., IgG, IgM, IgA, IgD or IgE) and includes monoclonal, recombinant, polyclonal, monoclonal, recombinant, polyclonal, chimeric, human, and humanized molecules of this type. Monoclonal antibodies may be produced by a eukaryotic cell clone expressing an antibody. Monoclonal antibodies may also be produced by a eukaryotic cell line which can recombinantly express the heavy chain and light chain of the antibody by virtue of having nucleic acid sequences encoding these introduced into the cell. Methods to produce antibodies from different eukaryotic cell lines such as Chinese Hamster Ovary (CHO) cells, hybridomas or immortalized antibody cells derived from an animal (e.g., human) are well known.

An antibody may be derived from rat, mouse, primate (e.g., cynomolgus, Old World monkey or Great Ape), human or other sources such as nucleic acids generated using molecular biology techniques which encode an antibody molecule.

An antibody may comprise a constant region, which may be of any isotype or subclass. The constant region may be of the IgG isotype, for example, IgG$_1$, IgG$_2$, IgG$_3$, IgG$_4$ or variants thereof. The antigen binding protein constant region may be IgG$_1$.

The antigen binding protein may comprise one or more modifications selected from a mutated constant domain such that the antibody has enhanced effector functions/ADCC and/or complement activation.

An antibody may be capable of binding to a target antigen. Examples, of such target antigens include human IL-5 comprising the amino acid sequence shown in SEQ ID NO: 11.

The terms "antibody variant" or "variant form" as used herein means an antibody that differs from a parent antibody by virtue of at least one amino acid modification (e.g., by having a different amino acid side chain), post-translational modification or other modification in at least one heavy chain, light chain, or combinations of these that results in a structural change (e.g., different amino acid side chain, different post-translational modification or other modification) relative to the parent antibody. 28Y042-7F11-1 is an example of a such a parent antibody. Structural changes can be determined directly by a variety of methods well know in the art such as LC-MS, direct sequencing or indirectly via methods such as isoelectric focusing and the like. Such methods are well known to those of ordinary skill in the art.

The term "IL-5" as used herein means human IL-5 comprising the amino acid sequence shown in SEQ ID NO: 11.

The term "specifically binds", as used herein in relation to antigen binding proteins means that the antigen binding protein binds to a target antigen as well as a discrete domain, or discrete amino acid sequence, within a target antigen with no or insignificant binding to other (for example, unrelated) proteins. This term, however, does not exclude the fact that the antigen binding proteins may also be cross-reactive with closely related molecules (for example, those with a high degree of sequence identity or from another genera or species). The antigen binding proteins described herein may bind to human IL-5 or the human IL-5 receptor with at least 2, 5, 10, 50, 100, or 1000-fold greater affinity than they bind to closely related molecules.

The binding affinity ($K_D$) of the antigen binding protein-target antigen interaction may be 1 mM or less, 100 nM or less, 10 nM or less, 2 nM or less or 1 nM or less. Alternatively, the $K_D$ may be between 5 and 10 nM; or between 1 and 2 nM. The $K_D$ may be between 1 pM and 500 pM; or between 500 pM and 1 nM. The binding affinity of the antigen binding protein is determined by the association constant (Ka) and the dissociation constant (Kd) ($K_D$=Kd/Ka). The binding affinity may be measured by BIACORE™, for example, by capture of the test antibody onto a protein-A coated sensor surface and flowing target antigen over this surface. Alternatively, the binding affinity can be measured by FORTEBIO, for example, with the test antibody receptor captured onto a protein-A coated needle and flowing target antigen over this surface.

The $K_d$ may be $1\times10^{-3}$ Ms$^{-1}$ or less, $1\times10^{-4}$ Ms$^{-1}$ or less, or $1\times10^{-5}$ Ms$^{-1}$ or less. The $K_d$ may be between $1\times10^{-5}$ Ms$^{-1}$ and $1\times10^{-4}$ Ms$^{-1}$; or between $1\times10^{-4}$ Ms$^{-1}$ and $1\times10^{-3}$ Ms$^{-1}$. A slow $K_d$ may result in a slow dissociation of the antigen binding protein-target antigen complex and improved neutralization of the target antigen.

The term "specific antigen binding activity" as used herein means antigen binding activity as measured by Surface Plasmon Resonance (SPR). IL-5 specific binding activity may be determined by SPR using a BIACORE™ instrument, for example performed in the binding mode. It is binding activity divided by total protein (e.g., 28Y042-7F11-1) content in a sample.

The term "FcRn binding activity" as used herein means Neonatal Fc (FcRn) Receptor binding activity as measured by Surface Plasmon Resonance (SPR). FcRn binding may be determined using a BIACORE™ instrument. It is binding activity to the FcRn receptor, divided by the total protein concentration of the sample.

The SPR method for specific antigen binding and FcRn binding uses a reference standard of 28Y042-7F11-1. The 28Y042-7F11-1 reference standard can be used in assays to obtain system suitability and sample comparability data, to ensure methods are performing appropriately. The reference standard can allow the establishment of a calibration curve and concentrations of the samples are interpolated from the curve.

By "isolated", it is intended that the molecule, such as an antigen binding protein or nucleic acid, is removed from the environment in which it may be found in nature. For example, the molecule may be purified away from substances with which it would normally exist in nature. For example, the mass of the molecule in a sample may be 95% of the total mass. The disclosure also provides isolated nucleic acids comprising SEQ ID NO:s 13, 14, 15, 16, 17 and/or 18 and portions thereof as well as compositions of these. Importantly, the disclosed nucleic acid can typically be provided as composition comprising any combination of the disclosed nucleic acids, buffer, residual buffer, salts, counter ions, water, alcohols or vector and the like.

The terms "$V_H$" and "$V_L$" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least one CDR and wherein the at least one CDR is CDRH3. Framework regions follow each of these CDR regions. Acceptable heavy chain variable region and light chain variable region framework 1, framework 2 and framework 3 regions are readily recognized by those of ordinary skill in the art. Acceptable heavy chain constant regions (including hinge regions) and light chain constant regions are readily recognized by those of ordinary skill in the art as well. Acceptable antibody isotypes are similarly readily recognized by those of ordinay skill in the art.

In this specification, amino acid residues in variable domain sequences and full length antibody sequences may be numbered according to the Kabat numbering convention. Similarly, the terms "CDR", "CDRL1", "CDRL2", "CDRL3", "CDRH1", "CDRH2", "CDRH3" used in the specification follow the Kabat numbering convention.

It will be apparent to those skilled in the art that there are alternative numbering conventions for amino acid residues in variable domain sequences and full length antibody sequences. There are also alternative numbering conventions for CDR sequences, for example those set out according to the Chothia numbering convention. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Residue positions in variant forms of an antibody herein are described with reference to the sequentially numbered residue positions in a given amino acid sequence.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE

| | Kabat CDR | Chothia CDR | AbM CDR | Contact CDR | Minimum binding unit |
|---|---|---|---|---|---|
| H1 | 31-35/ 35A/ 35B | 26-32/ 33/34 | 26-35/ 35A/ 35B | 30-35/ 35A/ 35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

"Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query sequence may be described by a nucleic acid sequence identified in one or more claims herein.

Nucleic acid sequences which may be useful, and included, in the compositions and related methods of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the nucleic acid sequences identified in the disclosure (e.g., nucleic acids encoding an antibody heavy chain or antibody light chain). In the disclosure, percent identity between the nucleic acid sequences described may include any discrete subrange of the percent identity ranges recited above (e.g., any range of integer values within a particular range or discrete subvalues within a particular range).

"Percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query sequence may be described by an amino acid sequence identified in one or more claims herein.

The amino acid sequences which may be useful, and included, in compositions of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the amino acid sequences identified in the disclosure (e.g., to an antibody heavy chain or antibody light chain). In the disclosure, percent identity between the amino acid sequences described may include any discrete subrange of the percent identify ranges recited above (e.g., any range of integer values within a particular range or discrete subvalues within a particular range). Amino acid sequences in the compositions of the disclosure may also include peptide chains (e.g., antigen binding proteins such as antibodies) comprising one or more CDRS of a first antibody, first variant, second variant or third variant of the disclosure. The disclosure also describes antigen binding proteins such as antibodies comprising the first variant, second variant and/or third variants—alone or in combination with each other (e.g., each of these variants alone, each possible pairing of these, or the triple combination of these as well) and supports claims to such antibodies and compositions comprising such antibodies. Additionally, the disclosure describes individual variant antibody species. Such individual variant antibody species described herein are apparent from the description of the first variant, second variant and third variants of the disclosure (e.g., from the description of the first variant a description of a variant antibody species comprising a heavy chain having at least one serine residue at position 60 of SEQ ID NO: 1 and the light chain of SEQ ID NO: 2 can be seen etc.) and claims to such antibodies and compositions comprising such antibodies are supported by the disclosure. Such variants are believed to be useful in human IL-5 binding antibody compositions including pharmaceutical compositions.

The terms "peptide", "polypeptide", "protein" and "peptide chain" each refer to a molecule comprising two or more amino acid residues. A peptide may be monomeric or polymeric.

It is well recognized in the art that certain amino acid substitutions are regarded as being "conservative". Amino acids are divided into groups based on common side-chain properties and substitutions within groups that maintain all or substantially all of the binding affinity of the antigen binding protein are regarded as conservative substitutions. See Table 2. The antigen binding proteins disclosed herein can comprise such "conservative" amino acid substitutions.

TABLE 2

| Side chain | Members |
| --- | --- |
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

The term "pharmaceutical composition" as used herein means a composition suitable for administration to a patient.

The pharmaceutical compositions described herein may comprise purified preparations of a composition as described herein.

For example, the pharmaceutical preparation may comprise a purified preparation of a composition as described herein in combination with a pharmaceutically acceptable carrier.

Typically, such pharmaceutical compositions comprise a pharmaceutically acceptable carrier as known and called for by acceptable pharmaceutical practice. Examples of such carriers include sterilized carriers, such as saline, Ringers solution, or dextrose solution, optionally buffered with suitable buffers to a pH within a range of 5 to 8.

Pharmaceutical compositions may be administered by injection or infusion (e.g., intravenous, intraperitoneal, intradermal, subcutaneous, intramuscular, or intraportal). Such compositions are suitably free of visible particulate matter. Pharmaceutical compositions may comprise between 1 mg to 10 g of antigen binding protein, for example, between 5 mg and 1 g of antigen binding protein. Alternatively, the composition may comprise between 5 mg and 500 mg of antigen binding protein, for example, between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilized (freeze dried) for reconstitution prior to administration according to methods well known or apparent to those skilled in the art. Where antibodies have an $IgG_1$ isotype, a chelator of copper, such as citrate (e.g., sodium citrate) or EDTA or histidine, may be added to the pharmaceutical composition to reduce the degree of copper-mediated degradation of antibodies of this isotype. Pharmaceutical compositions may also comprise a solubilizer, such as arginine, a surfactant/anti-aggregation agent such as polysorbate 80, and an inert gas such as nitrogen to replace vial headspace oxygen.

One aspect of the disclosure is a composition comprising a) a first antibody having a heavy chain amino acid sequence as shown in SEQ ID NO: 1 and a light chain amino acid sequence shown in SEQ ID NO: 2; and b) a first variant form of the first antibody comprising at least one serine residue at a position selected from the group consisting of position 60 of SEQ ID NO: 1, position 317 of SEQ ID NO: 1 and position 363 of SEQ ID NO: 1.

Another aspect of the disclosure is a composition comprising a) a first antibody having a heavy chain amino acid sequence as shown in SEQ ID NO: 1 and a light chain amino acid sequence shown in SEQ ID NO: 2; and b) a second variant form of the first antibody comprising at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; and b) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a first variant form of the first antibody comprising at least one serine residue at a position selected from the group consisting of position 60 of SEQ ID NO: 1, position 317 of SEQ ID NO: 1 and position 363 of SEQ ID NO: 1; and c) a second variant form of the first antibody comprising at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a first variant form of the first antibody comprising at least one serine residue at a position selected from the group consisting of position 60 of SEQ ID NO: 1, position 317 of SEQ ID NO: 1 and position 363 of SEQ ID NO: 1; and c) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a second variant form of the first antibody comprising at least one serine residue at a position selected from the group consisting of position 22 of SEQ ID NO: 2, position 37 of SEQ ID NO: 2 and position 216 of SEQ ID NO: 2; and c) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

Another aspect of the disclosure is a composition comprising a) a first antibody having a heavy chain amino acid sequence as shown in SEQ ID NO: 1 and a light chain amino acid sequence shown in SEQ ID NO: 2; b) a first variant form of the first antibody comprising at least one serine residue at a position selected from the group consisting of position 60 of SEQ ID NO: 1, position 317 of SEQ ID NO: 1 and position 363 of SEQ ID NO: 1; c) a second variant form of the first antibody comprising at least one serine residue at a position selected from the group consisting of position 22 of SEQ ID NO: 2, position 37 of SEQ ID NO: 2 and position 216 of SEQ ID NO: 2; and d) a third variant form of the first antibody comprising at least one serine residue at a position selected from the group consisting of position 60 of SEQ ID NO: 1, position 317 of SEQ ID NO: 1 and position 363 of SEQ ID NO: 1, and at least one serine residue at a position selected from the group consisting of position 22 of SEQ ID NO: 2, position 37 of SEQ ID NO: 2 and position 216 of SEQ ID NO: 2.

In an embodiment of the composition of the disclosure the first variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO: 1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1 and position 436 of SEQ ID NO: 1.

In an embodiment of the composition of the disclosure the second variant form further comprises at least one serine residue at a position selected from the group consisting of position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2.

In an embodiment of the composition of the disclosure the third variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO: 1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1, position 436 of SEQ ID NO: 1, position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2.

In an embodiment of the composition of the disclosure the first variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO: 1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1 and position 436 of SEQ ID NO: 1; and the second variant form further comprises at least one serine residue at a position selected from the group consisting of position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2.

In an embodiment of the composition of the disclosure the first variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO: 1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1 and position 436 of SEQ ID NO: 1; and the third variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO: 1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1, position 436 of SEQ ID NO: 1, position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2.

In an embodiment of the composition of the disclosure the second variant form further comprises at least one serine residue at a position selected from the group consisting of position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2; and the third variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO:

1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1, position 436 of SEQ ID NO: 1, position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2.

In an embodiment of the composition of the disclosure the first variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO: 1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1 and position 436 of SEQ ID NO: 1; the second variant form further comprises at least one serine residue at a position selected from the group consisting of position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2; and the third variant form further comprises at least one serine residue at a position selected from the group consisting of position 76 of SEQ ID NO: 1, position 84 of SEQ ID NO: 1, position 161 of SEQ ID NO: 1, position 203 of SEQ ID NO: 1, position 205 of SEQ ID NO: 1, position 210 of SEQ ID NO: 1, position 278 of SEQ ID NO: 1, position 288 of SEQ ID NO: 1, position 386 of SEQ ID NO: 1, position 391 of SEQ ID NO: 1, position 392 of SEQ ID NO: 1, position 423 of SEQ ID NO: 1, position 436 of SEQ ID NO: 1, position 31 of SEQ ID NO: 2, position 34 of SEQ ID NO: 2, position 143 of SEQ ID NO: 2, position 144 of SEQ ID NO: 2, position 158 of SEQ ID NO: 2 and position 164 of SEQ ID NO: 2.

It is preferred the compositions of the disclosure comprise less than 5%, 4%, 3%, 2%, 1%, 0.9%, 0.8%, 0.7%, 0.6%, 0.5%, 0.4%, 0.3%, 0.2%, 0.1%, 0.05% or 0.005% variant antibody (e.g., the percentage of the first variant form, second variant form and/or third variant form alone and/or in combination is less than these percentages where this percentage is expressed relative to the total amount of both first antibody and variant antibody present in a composition). In the disclosure, a range such as less than 5% (e.g., from 5% to 0%) may include any discrete subrange of the ranges recited (e.g., any range of integer values within a particular range or discrete subvalues within a particular range).

An embodiment of the disclosure is a pharmaceutical composition comprising a pharmaceutically acceptable carrier and a composition according to the disclosure.

The compositions described herein may be produced by any number of conventional techniques. For example, the compositions may be expressed in and purified from recombinant expression systems. The composition may also be produced by a method of culturing a host cell under conditions suitable for expression of a polypeptide comprising SEQ ID NO: 1 and SEQ ID NO:2 and a variant form of this antibody, followed by purification, and formulation within a pharmaceutical composition.

A number of different expression systems and purification regimes can be used to produce the compositions. Generally, host cells are transformed with a recombinant expression vector encoding the antibody. A wide range of host cells can be employed, including eukaryotic cell lines of mammalian origin (e.g., CHO, Perch, HEK293, HeLa, NSO). Suitable host cells include mammalian cells such as CHO (e.g., CHOK1 and CHO-DG44) and include CHO cells deficient in glutamine synthetase.

The host cell may be an isolated host cell. The host cell is usually not part of a multicellular organism (e.g., plant or animal). The host cell may be a non-human host cell.

Appropriate cloning and expression vectors for use with eukaryotic or mammalian cellular hosts and methods of cloning are known in the art.

The cells may be cultured under conditions that promote expression of the antibody. For example, a production bioreactor is used to culture the cells. The production bioreactor volume may be: (i) about 20,000 litres, about 10,000 litres; about 5,000 litres; about 2,000 litres; about 1,000 litres; or about 500 litres; or (ii) between 500 and 20,000 litres; between 500 and 10,000 litres; between 500 and 5,000 litres; between 1,000 and 10,000 litres, or between 2,000 and 10,000 litres. For example, the cells may be cultured in a production bioreactor at a pH of about 6.75 to pH 7.00. Alternatively, the cells may be cultured in a production bioreactor for about 12 to about 18 days. Alternatively, the cells may be cultured in a production bioreactor at a pH of about 6.75 to pH 7.00, for about 12 to about 18 days. This culture step may help to control the level of deamidated antibody variants, for example, to reduce the level of deamidated antibody variants.

Many different culture mediums suitable for the growth of eukaryotic cells expressing antibodies and useful in the preparation of the compositions of the disclosure are also known in the art. Such mediums include, for example, minimal essential medium supplemented with fetal bovine serum and chemically defined mediums. HL-1™ chemically defined, serum-free medium for eukaryotic cell cell culture is an example of such a chemically defined medium. HL-1™ media is commercially available from Lonza. Those skilled in the art will recognize many other chemically defined growth mediums suitable for the preparation of the compositions of the disclosure. Many such growth mediums are commercially available as well.

The composition of the disclosure may be recovered and purified by conventional protein purification procedures. For example, the composition may be harvested directly from the culture medium. Harvest of the cell culture medium may be via clarification, for example by centrifugation and/or depth filtration. Recovery of the composition is followed by purification to ensure adequate purity.

One or more chromatography steps may be used in purification, for example one or more chromatography resins; and/or one or more filtration steps. For example affinity chromatography using resins, such as protein A, G, or L may be used to purify the composition. Alternatively, or in addition to, an ion-exchange resin such as a cation-exchange may be used to purify the composition. Alternatively, or in addition to, a hydrophobic interaction chromatographic resin may be used to purify the composition. Alternatively the purification steps comprise: an affinity chromatography resin step, followed by a cation-exchange resin step, followed by a hydrophobic interaction chromatographic resin step.

For example, the harvest is placed in contact with a protein A resin. The solution comprising the composition may be eluted from the protein A resin and treated at pH 3.3 to 3.7 for 15 to 240 minutes. This protein A resin step may help to control the level of aggregated antibody variants, for example, to reduce the level of aggregated antibody variants.

The solution comprising the composition may then be further clarified by depth filtration and/or dual layer filtration.

Alternatively, or in addition to, an anion exchange resin may be used. The solution comprising the composition may be placed in contact with an anion exchange resin (for example Q-SEPHAROSE™ Fast Flow anion exchange chromatography) at a load pH of 8.3 to 8.7. The solution comprising the composition may be eluted from the anion exchange resin and held for 96 hours or less. This anion exchange resin step may help to control the level of deamidated antibody variants, for example, to reduce the level of deamidated antibody variants.

Optionally, guanidine and/or ammonium sulphate may be added to the solution comprising the composition, and held for 15 to 240 minutes.

Alternatively, or in addition to, a hydrophobic interaction chromatographic resin may be used. The solution comprising the composition may be placed in contact with a hydrophobic interaction chromatographic resin (e.g., phenyl SEPHAROSE™ fast flow chromatography) at a load ratio of 12 to 27 g protein/L resin. For example, the solution comprising the composition may be eluted using an elution gradient volume (bed volumes; BV) of about 9 to about 11. An elution peak cut stop (% of maximum peak height) of about 17 to about 23 may be used during elution from the hydrophobic interaction chromatographic resin. This hydrophobic interaction chromatographic resin step may help to control the level of aggregated antibody variants, for example, to reduce the level of aggregated antibody variants.

The solution comprising the composition may then be filtered to remove virus. The solution comprising the composition may then be formulated at an antibody concentration of about 76 g protein/L to about 82 g protein/L, or to about 100 g protein/L. The solution comprising the composition may be filled into containers and frozen. Aliquots of the solution comprising the composition may be lyophilized. Lyophilizate may be reconstituted by the addition of water to produce a composition comprising 75 mg/L of protein, the monoclonal anti-IL-5 antibody and 20 mM sodium phosphate dibasic heptahydrate, 12% weight of sucrose to volume and 0.05% weight of polysorbate 80 to volume at a pH of from about 6.8 to about 7.2.

The compositions of the disclosure can also be made by expressing and purifying a first antibody comprising SEQ ID NO: 1 and SEQ ID NO: 2, separately expressing and purifying a variant antibody of the disclosure and then combining the first antibody and the variant antibody to produce a composition of the disclosure.

For example, the nucleic acid of SEQ ID NO: 13 and the nucleic acid of SEQ ID NO: 14 can be co-expressed in a eukaryotic cell (such as a glutamine synthetase deficient CHO cell grown under standard conditions in a chemically defined medium) to produce an antibody comprising the heavy chain amino acid sequence as shown in SEQ ID NO: 1 and the light chain nucleic acid sequence as shown in SEQ ID NO: 2 (i.e., a first antibody). The nucleic acid of SEQ ID NO: 13 can then be modified to encode a variant heavy chain of the disclosure. For example, the codon in SEQ ID NO: 13 encoding the amino acid residue at position 317 of SEQ ID NO: 1 can be modified to encode a variant heavy chain comprising a serine residue at this position. This can be done, for example, by replacing the appropriate codon in SEQ ID NO: 13 with a "tct", "tcc", "tca", "tcg", "agt" or "agc" codon encoding serine. The resulting modified nucleic acid (with appropriate start codons, leader sequences, etc.) encoding this variant heavy chain can then be co-expressed with the nucleic acid of SEQ ID NO: 14 in a eukaryotic cell (such as a glutamine synthetase deficient CHO cell) to produce an antibody comprising a first variant form antibody of the disclosure (e.g., a first variant form of the first antibody). These separately produced preparations of a first antibody and a first variant antibody can then be combined to produce the compositions of the disclosure. It is preferred the compositions of the disclosure comprise less than 5%, 4%, 3%, 2%, 1%, 0.9%, 0.8%, 0.7%, 0.6%, 0.5%, 0.4%, 0.3%, 0.2%, 0.1%, 0.05% or 0.005% variant antibody (e.g., the percentage of the first variant form, second variant form and/or third variant form alone and/or in combination is less than these percentages where this percentage is expressed relative to the total amount of both first antibody and variant antibody present in a composition). In the disclosure, a range such as less than 5% (e.g., from 5% to 0%) may include any discrete subrange of the ranges recited (e.g., any range of integer values within a particular range or discrete subvalues within a particular range).

Importantly, the nucleic acid sequences shown in SEQ ID NO: 24 and SEQ ID NO: 25 can be modified to produce any first antibody, first variant form, second variant form and third variant form of the disclosure. This can be done by replacing the appropriate "nnn" residue(s) in these sequences with a serine codon and/or with a codon encoding the corresponding amino acid residue found at that position in either the heavy chain of SEQ ID NO: 1 (for SEQ ID NO: 24) and/or the light chain of SEQ ID NO 2 (for SEQ ID NO: 25). Such nucleic acid sequences may then be used to produce the compositions of the disclosure as described above.

EXAMPLES

Example 1

Characterization of Compositions Comprising Antibody Variants

Compositions comprising the 28Y042-7F11-1 antibody were produced by recombinant expression from eukaryotic cells containing a nucleic acid encoding the 28Y042-7F11-1 antibody heavy chain (SEQ ID NO: 1) and a nucleic acid encoding the 28Y042-7F11-1 antibody light chain (SEQ ID NO: 2). Four different sets of culture conditions were used for the production of compositions comprising the 28Y042-7F11-1 antibody. Standard antibody purification methods were used to prepare four compositions comprising the 28Y042-7F11-1 antibody. These four compositions were then characterized by LC-MS/(MS) analytical techniques. The four compositions comprising the 28Y042-7F11-1 antibody were a Reference Standard (RS) preparation, a Mini Reactor (MR) preparation, a Test Material™ preparation and a Tangential Flow (TF) preparation.

The reference standard (RS) composition was produced by culture in a bioreactor (production bioreactor) from CHO cells lacking glutamine synthetase (GS). These cells were stably transfected with expression vector constructs encoding the 28Y042-7F11-1 antibody heavy chain amino acid sequence shown in SEQ ID NO: 1 (e.g., encoded by SEQ ID NO: 13 or a nucleic acid comprising SEQ ID NO: 14) and the 28Y042-7F11-1 light chain amino acid sequence shown in SEQ ID NO: 2 (e.g., encoded by SEQ ID NO: 15 or a nucleic acid comprising SEQ ID NO: 18). Culture conditions were as follow: The initial culture medium comprised 70% (v/v) CD CHO medium (chemically defined, protein-free basal medium commercially available from Invitrogen) and 30% (v/v) EFFICIENTFEED™ B (a chemically defined, protein-free feed medium commercially available from Invitrogen) supplemented with amino acids. The production bioreactor was inoculated at a starting cell density of 0.5×10⁶ cells/mL iVCC (initial viable cell concentration). The culture was then fed at 10% (v/v) of the initial working volume at inoculation of the production bioreactor with the amino acid supplemented EFFICIENTFEED™ B. Feeding was on days 3, 6, 9, 13 and 15. The culture conditions were maintained at 35° C. (this was the process temperature through the entire production run), a pH from 6.95 to 7.2 (the culture starting pH was 7.2 +/1 0.15 and shifted on Day 3 to pH 6.95 +/−0.05 through the remainder of the production run) and a dissolved oxygen level of 30% was maintained through the entire production run.

The mini reactor (MR) composition was produced by culture from CHO cells lacking glutamine synthetase (GS). These cells were stably transfected with expression vector constructs encoding the 28Y042-7F11-1 antibody heavy chain amino acid sequence shown in SEQ ID NO: 1 (e.g., encoded by SEQ ID NO: 13 or a nucleic acid comprising SEQ ID NO: 14) and the 28Y042-7F11-1 light chain amino acid sequence shown in SEQ ID NO: 2 (e.g., encoded by SEQ ID NO: 15 or a nucleic acid comprising SEQ ID NO: 18). Culture conditions were as follow: The initial culture medium was a chemically defined, animal origin free, hydrolysate free medium. The feed medium was a chemically defined medium hydrated from powder to a 1× concentration (i.e., to the normal dilution) and amino acid supplemented. The mini reactor was inoculated at a starting cell density of 0.5×10⁶ cells/mL iVCC. The culture was fed on days 3, 6, 8, 10 and 13 with an appropriate volume of culture medium (e.g., an amount consistent with the mini-reactor volume and this number of feedings in a fed batch format). The culture conditions were maintained at 35° C. (this was the process temperature through the entire production run), a pH from 6.95 to 7.2 (the culture starting pH was 7.2 +11 0.15 and shifted on Day 3 to pH 6.95 +/−0.05 through the remainder of the production run) and a dissolved oxygen level of 30% was maintained through the entire production run.

The test material (TM) composition was produced from CHO cells lacking glutamine synthetase (GS). These cells were stably transfected with expression vector constructs encoding the 28Y042-7F11-1 antibody heavy chain amino acid sequence shown in SEQ ID NO: 1 (e.g., encoded by SEQ ID NO: 13 or a nucleic acid comprising SEQ ID NO: 14) and the 28Y042-7F11-1 light chain amino acid sequence shown in SEQ ID NO: 2 (e.g., encoded by SEQ ID NO: 15 or a nucleic acid comprising SEQ ID NO: 18). The initial culture medium was a chemically defined, animal origin free, hydrolysate free medium. Culture conditions were as follow: The initial culture medium was a chemically defined, animal origin free, hydrolyslate free medium. The fed medium was a chemically defined medium which was hydrated from powder to a 3× concentration (relative to the normal 1× dilution) and amino acid supplemented. The bioreactor was inoculated at a starting cell density of 1×10⁶ cells/mL iVCC (initial viable cell concentration). The culture was fed on days 0, 3, 6, 8, 10, 12 and 14 amino acid supplemented medium; on days 3, 6, 8, 10, 12 and 14 the culture was fed with an amino acid supplement; and on day 3 the culture was feed with a tracemetal solution give as a single solution on day 3. The culture conditions were maintained at 35° C. (this was the process temperature through the entire production run), a pH from 6.95 to 7.2 (the culture starting pH was 7.2+11 0.15 and shifted on Day 3 to pH 6.95 +/−0.05 through the remainder of the production run) and a dissolved oxygen level of 30% was maintained through the entire production run.

The tangential flow bulk drug substance (TF) composition was produced from CHO cells lacking glutamine synthetase (GS). These cells were stably transfected with expression vector constructs encoding the 28Y042-7F11-1 antibody heavy chain amino acid sequence shown in SEQ ID NO: 1 (e.g., encoded by SEQ ID NO: 13 or a nucleic acid comprising SEQ ID NO: 14) and the 28Y042-7F11-1 light chain amino acid sequence shown in SEQ ID NO: 2 (e.g., encoded by SEQ ID NO: 15 or a nucleic acid comprising SEQ ID NO: 18). Culture conditions were as follow: The initial culture medium was a chemically defined, animal origin free, hydrolyslate free medium. The feed medium was a chemically defined medium which was hydrated from powder to a 1× concentration (i.e., to the normal dilution). The reactor was inoculated at a starting cell density of 15×10⁶ cells/mL iVCC. This inoculum was prepared in a bioreactor by perfusion culture of the cells where the culture medium was a chemically defined, animal origin free, hydrolyslate free medium. This inoculum culture bioreactor was fitted with a tangential flow filter which functioned to retain cells in the bioreactor as perfusion occurred. The inoculum culture conditions were maintained at 37° C., at about pH 6.95 +/−0.05 and a dissolved oxygen level of 50%. The inoculated production bioreactor has then provided with feed medium at a 0.004 pL/cell/minute. The production culture conditions were maintained at 33° C. (this was the process temperature through the entire production run), about pH 6.95 +/−0.05 (throughout the entire production run) and a dissolved oxygen level of 50% was maintained through the entire production run.

Samples of the RS, MR, TM and TF compositions were then prepared for liquid chromatography-tandem mass spectrometry (LC-MS/(MS)) analysis. 250 μg of each of these protein samples were dried in a SPEEDVAC™ with no heat. Then 60 μL of denaturing buffer (6 M guanidine hydrochloride, 1.2 M Tris/HCl, 2.5 mM Na₂EDTA, pH 7.5) was added to each dried sample, followed by addition of 3 μL of freshly prepared 1 M DTT. Samples were then reduced at room temp for 20 minutes. 14.4 μL of freshly prepared 0.5M iodoacetic acid-1-¹³C was then added to the reduced samples and alkylation was performed by incubation at room temperature in the darkness for 30 minutes. The alkylation reaction was terminated by adding 4.2 μL of 1 M DTT. Next, samples were buffer exchanged with digestion buffer (50 mM Tris/HCl, 1 mM CaCl₂, pH 7.5) using BIORAD BIO-SPIN™ columns. Afterwards, 2.5 μL of solution containing 5 mg/ml freshly prepared trypsin was added to each sample for an enzyme to sample (E/S) ratio of 1:20. Samples were then trypsin digested by incubation at 37° C. for 25 minutes. Digestions were stopped by adding 3 μL of 1 M HCl.

LC-MS/(MS) analyses were then conducted as follows. First, 5 μL of digested peptide mixture was injected for reverse phase LC-MS/(MS) analysis. Separations were performed on a VANQUISH™ UPLC (Thermo Scientific) with a ACQUITY CSH™ C18, 2.1×150 mm, 1.7 μm column (Waters) using a linear gradient (0-60 min, 0 (100% Mobile Phase A) transitioning via linear gradient to 38% Mobile Phase B). Mobile phase A was water with 0.1% (v/v) formic acid (this was a dilution of a 98-100% formic acid solution). Mobile phase B was acetonitrile with 0.1% (v/v) formic acid (also a dilution of a 98-100% formic acid solution). The column temperature was maintained at 30° C. The flow rate was set at 0.2 mL/min.

MS analyses were performed upon UV detection, at 215 nm, of peptide containing fractions in the column eluate. A Q EXACTIVE PLUS™ hybrid quadrupole-ORBITRAP™ mass spectrometer (Thermo Scientific) capable of high resolution mass detection was used for these analyses.

This instrument permitted detection and differentiation of 28Y042-7F11-1 heavy chain peptide fragments and 28Y042-7F11-1 light chain fragments in the RS (IRS), MR, TM (CTM) and TF (ATF) compositions. Such peptide fragments correspond to portions of the 28Y042-7F11-1 heavy chain amino acid sequence (SEQ ID NO: 1) and the 28Y042-7F11-1 light chain amino acid sequence (SEQ ID NO: 2).

This instrument also permitted the detection and differentiation of variant antibody heavy chain peptide fragments and variant antibody light chain peptide fragments present in the compositions. In other words, the instrument permitted detection of variant forms of the 28Y042-7F11-1 antibody (i.e., forms with altered light chain and heavy chain amino acid sequences).

Tune settings for this instrument were optimized for peptide analysis with spray voltage at 3.5 kV, a capillary temperature of 300° C. and S-lens radiofrequency (RF) level of 50. The full mass scan ranges were from m/z 200 to 2000 with resolution at 70,000. The data dependent acquisition mode was used for HCD-MS/MS (HCD: high energy collision dissociation) with a resolution of 17,500.

Data analysis was then performed using BYONIC™ and BYOLOGIC™ software (Protein Metrics). Search parameters used with this software were those suggested from the vendor's application notes. False positives of amino acid variation were removed by software filters and manual inspection. Missing peptides for certain samples in the search were added through the existing peptides. The final percentage of amino acid variation present was calculated by dividing the extracted ion current of the modified peptide by the summed extracted ion current of wild type and modified peptides.

LC-MS/(MS) analyses showed antibody variants containing serine residues at positions 60, 317 and 363 corresponding to the 28Y042-7F11-1 antibody heavy chain and at positions 22, 37 and 216 of the 28Y042-7F11-1 antibody light chain were present in the samples. These analyses also showed the unvaried heavy and light chains of the 28Y042-7F11-1 antibody were present in the samples as indicated in Table 3 (Table 3). Variant antibodies containing at least one serine residue in antibody peptide sequence fragments comprising positions 76, 84, 161, 203, 205, 210, 278, 288, 386, 391, 392, 423 and 436 corresponding to the 28Y042-7F11-1 antibody heavy chain were also present in the samples as indicated in Table 3. Similarly, variant antibodies containing at least one serine residue in antibody peptide sequence fragments comprising positions 31, 34, 143, 144, 158 and 164 corresponding to the 28Y042-7F11-1 antibody light chain were present in the samples as indicated in Table 3.

TABLE 3

| | | | Sample Names and Percentage of Antibody Fragment Variants Comprising a Serine Residue | | | |
|---|---|---|---|---|---|---|
| Protein Name | Peptide Sequence | Position | RS | MR | TM | TF |
| aIL5_EP Heavy Chain | DYFPEPVTVSWN$_{161}$SGALTSGVHT FPAVLQSSGLYSLSSVVTVPSSSL GTQTYICN$_{203}$VN$_{205}$HKPSN$_{210}$TK (SEQ ID NO: 26) | 161, 203, 205, 210 Relative to SEQ ID NO: 1 | 0.2 | 2.7 | 0.5 | 0.6 |
| aIL5_EP Heavy Chain | FN$_{278}$WYVDGVEVHN$_{288}$AK (SEQ ID NO: 27) | 278, 288 Relative to SEQ ID NO: 1 | 0.1 | 3.0 | 0.2 | 0.0 |
| aIL5_EP Heavy Chain | VVSVLTVLHQDWLN$_{317}$GK (SEQ ID NO: 28) | 317 Relative to SEQ ID NO: 1 | 0.1 | 1.8 | 0.1 | 0.0 |
| aIL_5EP Heavy Chain | N$_{363}$QVSLTCLVK (SEQ ID NO: 29) | 363 Relative to SEQ ID NO: 1 | 0.1 | 1.8 | 0.1 | 0.0 |
| aIL5_EP Heavy Chain | GFYPSDIAVEWESN$_{386}$GQPEN$_{391}$N$_{392}$YK (SEQ ID NO: 30) | 386, 391, 392 Relative to SEQ ID NO: 1 | 0.1 | 3.7 | 0.2 | 0.0 |
| aIL5_EP Heavy Chain | WQQGN$_{423}$VFSCSVMHEALHN$_{436}$HYTQK (SEQ ID NO: 31) | 423, 436 Relative to SEQ ID NO: 1 | 0.1 | 3.4 | 0.3 | 0.1 |

TABLE 3-continued

| Protein Name | Peptide Sequence | Position | Sample Names and Percentage of Antibody Fragment Variants Comprising a Serine Residue | | | |
|---|---|---|---|---|---|---|
| | | | RS | MR | TM | TF |
| aIL5_EP Heavy Chain | GLEWLGVIWASGGTDYN$_{60}$SALMSR (SEQ ID NO: 32) | 60 Relative to SEQ ID NO: 1 | 0.0 | 0.9 | 0.2 | 0.1 |
| aIL5_EP Heavy Chain | N$_{76}$QVVLTMTN$_{84}$MDPVDTATYYCAR (SEQ ID NO: 33) | 76, 84 Relative to SEQ ID NO: 1 | 0.0 | 2.0 | 0.2 | 0.0 |
| aIL5_EP Light Chain | SGTASVVCLLN$_{143}$N$_{144}$FYPR (SEQ ID NO: 34) | 143, 144 Relative to SEQ ID NO: 2 | 0.1 | 2.2 | 0.1 | 0.0 |
| aIL5_EP Light Chain | VDN$_{158}$ALQSGN$_{164}$SQESVTEQDSK (SEQ ID NO: 35) | 158, 164 Relative to SEQ ID NO: 2 | 0.1 | 3.6 | 0.2 | 0.0 |
| aIL5_EP Light Chain | SFN$_{216}$R (SEQ ID NO: 36) | 216 Relative to SEQ ID NO: 2 | 0.0 | 1.1 | 0.1 | 0.0 |
| aIL5_EP Light Chain to | ATIN$_{22}$CK (SEQ ID NO: 37) | 22 Relative SEQ ID NO: 2 | 0.0 | 1.3 | 0.1 | 0.0 |
| aIL5_EP Light Chain | SSQSLLN$_{31}$SGN$_{34}$QK (SEQ ID NO: 38) | 31, 34 Relative to SEQ ID NO: 2 | 0.1 | 2.6 | 0.1 | 0.0 |
| aIL5_EP Light Chain | N$_{37}$YLAWYQQKPGQPPK (SEQ ID NO: 39) | 37 Relative to SEQ ID NO: 2 | 0.0 | 1.3 | 0.1 | 0.0 |

Numbered positions in Table 3 correspond to the sequentially numbered positions shown in the 28Y042-7F11-1 antibody heavy chain (SEQ ID NO: 1) and the 28Y042-7F11-1 antibody light chain (SEQ ID NO: 2). This is also the case with the variant antibody heavy chain amino acid sequence shown in SEQ ID NO: 22 (where X may be a serine residue or a residue from the corresponding position of SEQ ID NO: 1) and the variant antibody light chain sequence shown in SEQ ID NO: 23 (where X may be a serine residue or a residue from the corresponding position of SEQ ID NO: 2). The Kabat and other antibody numbering conventions are not used in Table 3 to identify variant amino acid positions.

The prevelance of antibody variant fragments containing serine residues is also indicated in Table 3. For example, an antibody variant comprising a serine residue at position 317 of the heavy chain amino acid sequence is present in from 0.1% to 1.8% of the antibody molecules in the RS (IRS), MR (MR15) and TM (CTM) sample preparations of the 28Y042-7F11-1 antibody analyzed. The presence of these antibody variants was unexpected given that the nucleic acids expressed to produce the different samples did not encode these variants.

Example 2

Informal Sequence Listing

Underlining below identifies CDR sequences, according to the Kabat definition of CDRs, in the variable heavy and variable light chain portions of the antibodies or the nucleic acid sequences encoding these CDR sequences. For example, in SEQ ID NO: 1 the frameworks and CDRs are presented as plaintext framework1, underlined CDR1, plaintext framework2, underlined CDR2, plaintext framework3, underlined CDR3 and plaintext framework4 in order from the amino proximal portion to the carboxy terminal portion of the sequences presented. This scheme is used in SEQ ID NO:s 1-4 for example. Amino terminal methionine residues shown in these sequences can be cleaved. Thus, the sequences here showing an amino terminal methionine residue should also be considered to disclose the cleaved versions of these proteins lacking such an amino terminal methionine residue. Nucleic acids sequences are presented as DNA nucleic acid sequences and include "t" nucleic acid residues, the corresponding RNA sequence should also be considered as disclosed such that "t" nucleic acid residues may also be regarded as disclosing a "u" nucleic acid residue. Additionally, the 5' proximal "atg" start codon and the 3' proximal "taa," "tag," and "tga" stop codons have been omitted from the cDNA nucleic acid sequences below. "X" or "Xaa" as used herein refers to any amino acid residue such as, for example, a "S" or "N" amino acid residue. "n" as used herein refers to any nucleic acid residue and a "nnn" codon may encode any amino acid residue such as, for example, a "S" or "N" amino acid residue.

```
28Y042-7F11-1 FULL LENGTH HEAVY CHAIN
                                                                SEQ ID NO: 1
QVTLRESGPALVKPTQTLTLTCTVSGFSLTGSSVHWVRQPPGKGLEWLGVIWASGGT

DYNSALMSRLSISKDTSRNQVVLTMTNMDPVDTATYYCARDPPSGLLRLDYWGRGT

LVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKRVEPKSCDKTHTCP

PCPAPELLGGPSVFLFPPKPKDTLYITREPEVTCVVVDVSHEDPEVKFNWYVDGVEVH

NAKTKPREEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

28Y042-7F11-1 FULL LENGTH LIGHT CHAIN
                                                                SEQ ID NO: 2
DIVMTQSPDSLAVSLGERATINCKSSQSLLNSGNQKNYLAWYQQKPGQPPKWYGAS

TRESGVPDRFSGSGSGTDFTLTISSLQAEDVAVYYCQNVHSFPFTFGGGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

28Y042-7F11-1 VH
                                                                SEQ ID NO: 3
QVTLRESGPALVKPTQTLTLTCTVSGFSLTGSSVHWVRQPPGKGLEWLGVIWASGGT

DYNSALMSRLSISKDTSRNQVVLTMTNMDPVDTATYYCARDPPSGLLRLDYWGRGT

LVTVSS

28Y042-7F11-1 VL
                                                                SEQ ID NO: 4
DIVMTQSPDSLAVSLGERATINCKSSQSLLNSGNQKNYLAWYQQKPGQPPKWYGAS

TRESGVPDRFSGSGSGTDFTLTISSLQAEDVAVYYCQNVHSFPFTFGGGTKLEIKR

28Y042-7F11-1 CDRH1
                                                                SEQ ID NO: 5
GSSVH

28Y042-7F11-1 CDRH2
                                                                SEQ ID NO: 6
VIWASGGTDYNSALMS

28Y042-7F11-1 CDRH3
                                                                SEQ ID NO: 7
DPPSGLLRLDY

28Y042-7F11-1 CDRL1
                                                                SEQ ID NO: 8
KSSQSLLNSGNQKNYLA

28Y042-7F11-1 CDRL2
                                                                SEQ ID NO: 9
GASTRES

28Y042-7F11-1 CDRL3
                                                                SEQ ID NO: 10
QNVHSFPFT

HUMAN IL-5 (MATURE PROTEIN)
                                                                SEQ ID NO: 11
IPTEIPTSALVKETLALLSTHRTLLIANETLRIPVPVHKNHQLCTEEIFQGIGTLESQTVQ

GGTVERLFKNLSLIKKYIDGQKKKCGEERRRVNQFLDYLQEFLGVMNTEWIIES
```

HUMAN IL-5 RECEPTOR SUBUNIT ALPHA ISOFORM 1 (MATURE PROTEIN)
SEQ ID NO: 12

DLLPDEKISLLPPVNFTIKVTGLAQVLLQWKPNPDQEQRNVNLEYQVKINAPKEDDYE

TRITESKCVTILHKGFSASVRTILQNDHSLLASSWASAELHAPPGSPGTSIVNLTCTTNT

TEDNYSRLRSYQVSLHCTWLVGTDAPEDTQYFLYYRYGSWTEECQEYSKDTLGRNI

ACWFPRTFILSKGRDWLAVLVNGSSKHSAIRPFDQLFALHAIDQINPPLNVTAEIEGTR

LSIQWEKPVSAFPIHCFDYEVKIHNTRNGYLQIEKLMTNAFISIIDDLSKYDVQVRAAV

SSMCREAGLWSEWSQPIYVGNDEHKPLREWFVIVIMATICFILLILSLICKICHLWIKLF

PPIPAPKSNIKDLFVTTNYEKAGSSETEIEVICYIEKPGVETLEDSVF

DNA ENCODING 28Y042-7F11-1 FULL LENGTH HEAVY CHAIN WITH LEADER SEQUENCE
SEQ ID NO: 13 atgggctggtcctgcatcatcctgtttctggtggccaccgccaccggtgtgcacagccaggtgaccctgagggagagcggccccgcc ctggtgaagcccacacagaccctcactctgacctgcaccgtgagcggcttcagcctgaccggctctagcgtccactgggtgaggcag cccccgggcaagggcctggagtggctgggcgtgatctgggcaagcggggggacggactacaactcggccctgatgagcaggctct ccatcagcaaggacaccagccggaaccaggtggtgctgaccatgaccaacatggaccccgtggacaccgccacctattactgcgcc agggaccctccctccggccctgctgaggctggactactggggcaggggaacactagtgaccgtgtccagcgccagcaccaagggcc ccagcgtgttccccctggcccccagcagcaagagcaccagcggcggcacagccgccctgggctgcctggtgaaggactacttccc gagcccgtgaccgtgtcctggaacagcggagccctgaccagcggcgtgcacaccttccccgccgtgctgcagagcagcggcctgta cagcctgagcagcgtggtgaccgtgcccagcagcagcctgggcacccagacctacatctgtaacgtgaaccacaagcccagcaaca ccaaggtggacaagcgggtggagcccaagagctgtgacaagacccacacctgcccccctgccctgccccgagctgctgggagg ccccagcgtgttcctgttccccccaagcctaaggacaccctgtacatcaccagagaacccgaggtgacctgtgtggtggtggatgtga gccacgaggaccctgaggtgaagttcaactggtacgtggacggcgtggaggtgcacaatgccaagaccaagcccagggaggagca gtacaacagcacctaccgggtggtgtccgtgctgaccgtgctgcaccaggattggctgaacggcaaggagtacaagtgtaaggtgtcc aacaaggccctgcctgcccctatcgagaaaaccatcagcaaggccaagggccagcccagagagccccaggtgtacaccctgcccc ctagcagagaggagatgaccaagaaccaggtgtccctgacctgcctggtgaagggcttctaccccagcgacatcgccgtggagtgg gagagcaacggccagcccgagaacaactacaagaccacccccctgtgctggacagcgatggcagcttcttcctgtacagcaagctg accgtggacaagagcagatggcagcagggcaacgtgttcagctgctccgtgatgcacgaggccctgcacaatcactacacccagaa gagcctgagcctgtcccctggcaag DNA ENCODING 28Y042-7F11-1 FULL LENGTH LIGHT CHAIN WITH LEADER SEQUENCE
SEQ ID NO: 14 atgggctggtcctgcatcatcctgtttctggtggccaccgccaccggtgtgcacagcgacatcgtgatgacccagtctcccgattcactg gccgtgagcctgggcgagagggccaccatcaactgcaagagcagccagagcctcctgaacagcggcaaccagaagaactacctgg cctggtaccagcagaaacccggccagccccccaagctgctgatctatggcgcctccaccagggagagcggcgtgccagacaggttt agcggcagcggcagcggcaccgacttcaccctgacaatcagcagcctgcaggccgaggacgtggccgtgtactactgccagaacgt ccacagcttccccttcaccttcggcgggggaaccaagctggagatcaagcgtacggtggccgcccccagcgtgttcatcttcccccc agcgatgagcagctgaagagcggcaccgccagcgtggtgtgtctgctgaacaacttctaccccggggaggccaaggtgcagtggaa ggtggacaatgccctgcagagcggcaacagccaggagagcgtgaccgagcaggacagcaaggactccacctacagcctgagcag caccctgaccctgagcaaggccgactacgagaagcacaaggtgtacgcctgtgaggtgacccaccagggcctgtccagcccgtga ccaagagcttcaaccggggcgagtgc

DNA ENCODING 28Y042-7F11-1 HEAVY CHAIN VARIABLE REGION
SEQ ID NO: 15 caggtgaccctgagggagagcggccccgccctggtgaagcccacacagaccctcactctgacctgcaccgtgagcggcttcagcct gaccggctctagcgtccactgggtgaggcagcccccgggcaagggcctggagtggctgggcgtgatctgggcaagcggggggac ggactacaactcggccctgatgagcaggctctccatcagcaaggacaccagccggaaccaggtggtgctgaccatgaccaacatgg -continued acccccgtggacaccgccacctattactgcgccagggaccctcctccggcctgctgaggctggactactggggcaggggaacacta gtgaccgtgtccagc

DNA ENCODING 28Y042-7F11-1 LIGHT CHAIN VARIABLE REGION

SEQ ID NO: 16 gacatcgtgatgacccagtctcccgattcactggccgtgagcctgggcgagagggccaccatcaactgcaagagcagccagagcctc ctgaacagcggcaaccagaagaactacctggcctggtaccagcagaaacccggccagccccccaagctgctgatctatggcgcctc caccagggagagcggcgtgccagacaggtttagcggcagcggcagcggcaccgacttcaccctgacaatcagcagcctgcaggcc gaggacgtggccgtgtactactgccagaacgtccacagcttccccttcaccttcggcggggggaaccaagctggagatcaagcgt

DNA ENCODING 28Y042-7F11-1 FULL LENGTH HEAVY CHAIN

SEQ ID NO: 17 caggtgacccctgagggagagcggccccgccctggtgaagcccacacagaccctcactctgacctgcaccgtgagcggcttcagcct gaccggctctagcgtccactgggtgaggcagcccccggcaagggcctggagtggctgggcgtgatctgggcaagcggggggac ggactacaactcggccctgatgagcaggctctccatcagcaaggacaccagccggaaccaggtggtgctgaccatgaccaacatgg acccccgtggacaccgccacctattactgcgccagggaccctcctccggcctgctgaggctggactactggggcaggggaacacta gtgaccgtgtccagcgccagcaccaagggcccagcgtgttccccctggccccagcagcaagagcaccagcggcggcacagcc gccctgggctgcctggtgaaggactacttccccgagcccgtgaccgtgtcctggaacagcggagccctgaccagcggcgtgcacac cttccccgccgtgctgcagagcagcggcctgtacagcctgagcagcgtggtgaccgtgcccagcagcagcctgggcacccagacct acatctgtaacgtgaaccacaagcccagcaacaccaaggtggacaagcgggtggagcccaagagctgtgacaagacccacacctg cccccctgccctgcccccgagctgctgggaggcccccagcgtgttcctgttcccccccaagcctaaggacaccctgtacatcaccaga gaacccgaggtgacctgtgtggtggtggatgtgagccacgaggaccctgaggtgaagttcaactggtacgtggacggcgtggaggtg cacaatgccaagaccaagcccagggaggagcagtacaacagcacctacggggtggtgtccgtgctgaccgtgctgcaccaggattg gctgaacggcaaggagtacaagtgtaaggtgtccaacaaggccctgcctgccccatcgagaaaaccatcagcaaggccaagggcc agcccagagagccccaggtgtacaccctgccccctagcagagaggagatgaccaagaaccaggtgtccctgacctgcctggtgaag ggcttctaccccagcgacatcgccgtggagtgggagagcaacggccagcccgagaacaactacaagaccacccccctgtgctgga cagcgatggcagcttcttcctgtacagcaagctgaccgtggacaagagcagatggcagcagggcaacgtgttcagctgctccgtgatg cacgaggccctgcacaatcactacacccagaagagcctgagcctgtccctggcaag

DNA ENCODING 28Y042-7F11-1 FULL LENGTH LIGHT CHAIN

SEQ ID NO: 18 gacatcgtgatgacccagtctcccgattcactggccgtgagcctgggcgagagggccaccatcaactgcaagagcagccagagcctc ctgaacagcggcaaccagaagaactacctggcctggtaccagcagaaacccggccagccccccaagctgctgatctatggcgcctc caccagggagagcggcgtgccagacaggtttagcggcagcggcagcggcaccgacttcaccctgacaatcagcagcctgcaggcc gaggacgtggccgtgtactactgccagaacgtccacagcttccccttcaccttcggcggggggaaccaagctggagatcaagcgtacg gtggccgcccccagcgtgttcatcttcccccccagcgatgagcagctgaagagcggcaccgcagcgtggtgtgtctgctgaacaact tctaccccggggaggccaaggtgcagtggaaggtggacaatgccctgcagagcggcaacagccaggagagcgtgaccgagcagg acagcaaggactccacctacgcctgagcagcaccctgaccctgagcaaggccgactacgagaagcacaaggtgtacgcctgtgag gtgacccaccagggcctgtccagccccgtgaccaagagcttcaaccggggcgagtgc

28Y042-7F11-1 HEAVY CHAIN LEADER SEQUENCE

SEQ ID NO: 19

MGWSCIILFLVATATGVHS

28Y042-7F11-1 HEAVY CHAIN LEADER SEQUENCE

SEQ ID NO: 20

MGWSCIILFLVATATGVHS

28Y042-7F11-1 HEAVY CHAIN FR4 SEQUENCE

SEQ ID NO: 21

WGRGTLVTVSS

VARIANT ANTIBODY FULL LENGTH HEAVY CHAIN

SEQ ID NO: 22

QVTLRESGPALVKPTQTLTLTCTVSGFSLT<u>GSSVH</u>WVRQPPGKGLEWLG<u>VIWASGGT</u>
<u>DYXSALMS</u>RLSISKDTSRXQVVLTMTXMDPVDTATYYCAR<u>DPPSGLLRLDY</u>WGRGT
LVTVSSASTKGPSVFPLAPSSKSTSGGTAALGCLVKDYFPEPVTVSWXSGALTSGVHT
FPAVLQSSGLYSLSSVVTVPSSSLGTQTYICXVXHKPSXTKVDKRVEPKSCDKTHTCP
PCPAPELLGGPSVFLFPPKPKDTLYITREPEVTCVVVDVSHEDPEVKFXWYVDGVEVH
XAKTKPREEQYNSTYRVVSVLTVLHQDWLXGKEYKCKVSNKALPAPIEKTISKAKG
QPREPQVYTLPPSREEMTKXQVSLTCLVKGFYPSDIAVEWESXGQPEXXYKTTPPVLD
SDGSFFLYSKLTVDKSRWQQGXVFSCSVMHEALHXHYTQKSLSLSPGK

VARIANT ANTIBODY FULL LENGTH LIGHT CHAIN

SEQ ID NO: 23

DIVMTQSPDSLAVSLGERATIXC<u>KSSQSLLXSGXQKXYLA</u>WYQQKPGQPPKWY<u>GAS</u>
<u>TRES</u>GVPDRFSGSGSGTDFTLTISSLQAEDVAVYYC<u>QNVHSFPFT</u>FGGGTKLEIKRTVA
APSVFIFPPSDEQLKSGTASVVCLLXXFYPREAKVQWKVDXALQSGXSQESVTEQDS
KDSTYSLSSTLTLSKADYEKHKVYACEVTHQGLSSPVTKSFXRGEC

DNA ENCODING VARIANT ANTIBODY HEAVY CHAIN

SEQ ID NO: 24 caggtgaccctgagggagagcggccccgccctggtgaagcccacacagaccctcactctgacctgcaccgtgagcggcttcagcct
gaccggctctagcgtccactgggtgaggcagccccccggcaagggcctggagtggctgggcgtgatctgggcaagcgggggggac
ggactacnnntcggccctgatgagcaggctctccatcagcaaggacaccagccggnnncaggtggtgctgaccatgaccnnnatg
gaccccgtggacaccgccacctattactgcgccagggaccctccctccggcctgctgaggctggactactggggcaggggaacact
agtgaccgtgtccagcgccagcaccaaggccccagcgtgttccccctggccccagcagcaagagcaccagcggcggcacagc
cgccctgggctgcctggtgaaggactacttccccgagcccgtgaccgtgtcctggnnnagcggagccctgaccagcggcgtgcaca
ccttccccgccgtgctgcagagcagcggcctgtacagcctgagcagcgtggtgaccgtgcccagcagcagcctgggcacccagacc
tacatctgtnnngtgnnncacaagcccagcnnnaccaaggtggacaagcgggtggagcccaagagctgtgacaagacccacacct
gcccccctgccctgccccgagctgctggaggccccagcgtgttcctgttcccccccaagcctaaggacaccctgtacatcaccag
agaacccgaggtgacctgtgtggtggtggatgtgagccacgaggaccctgaggtgaagttcnnntggtacgtggacggcgtggagg
tgcacnnngccaagaccaagcccagggaggagcagtacaacagcacctaccgggtggtgtccgtgctgaccgtgctgcaccagga
ttggctgnnnggcaaggagtacaagtgtaaggtgtccaacaaggccctgcctgccccctatcgagaaaaccatcagcaaggccaagg
gccagcccagagagccccaggtgtacaccctgcccccctagcagagaggagatgaccaagnnncaggtgtccctgacctgcctggt
gaagggcttctaccccagcgacatcgccgtggagtgggagagcnnnggccagcccgagnnnnnntacaagaccacccccctgt
gctggacagcgatggcagcttcttcctgtacagcaagctgaccgtggacaagagcagatggcagcagggcnnngtgttcagctgctc
cgtgatgcacgaggccctgcacnnncactacacccagaagagcctgagcctgtcccctggcaag

DNA ENCODING VARIANT ANTIBODY LIGHT CHAIN

SEQ ID NO: 25 gacatcgtgatgacccagtctcccgattcactggccgtgagcctgggcgagagggccaccatcnnntgcaagagcagccagagcct
cctgnnnagcggcnnncagaagnnntacctggcctggtaccagcagaaaccggccagccccccaagctgctgatctatgcgcc
tccaccagggagagcggcgtgccagacaggtnagcggcagcggcagcggcaccgacttcaccctgacaatcagcagcctgcagg
ccgaggacgtggccgtgtactactgccagaacgtccacagcttccccttcaccttcggcgggggaaccaagctggagatcaagcgta
cggtggccgcccccagcgtgttcatcttcccccccagcgatgagcagctgaagagcggcaccgccagcgtggtgtgtctgctgnnnn
nnttctaccccgggaggccaaggtgcagtggaaggtggacnnngccctgcagagcggcnnnagccaggagcgtgaccgag
caggacagcaaggactccacctacagcctgagcagcaccctgaccctgagcaaggccgactacgagaagcacaaggtgtacgcct
gtgaggtgacccaccagggcctgtccagccccgtgaccaagagcttcnnncggggcgagtgc -continued

28Y042-7F11-1 HEAVY CHAIN FRAGMENT

DYFPEPVTVSWNSGALTSGVHTFPAVLQS SGLYSLSSVVTVPSSSLGTQTYICNVNHKPSNTK
SEQ ID NO: 26

28Y042-7F11-1 HEAVY CHAIN FRAGMENT

FNWYVDGVEVHNAK
SEQ ID NO: 27

28Y042-7F11-1 HEAVY CHAIN FRAGMENT

VVSVLTVLHQDWLNGK
SEQ ID NO: 28

28Y042-7F11-1 HEAVY CHAIN FRAGMENT

NQVSLTCLVK
SEQ ID NO: 29

28Y042-7F11-1 HEAVY CHAIN FRAGMENT

GFYPSDIAVEWESNGQPENNYK
SEQ ID NO: 30

28Y042-7F11-1 HEAVY CHAIN FRAGMENT

WQQGNVFSCSVMHEALHNHYTQK
SEQ ID NO: 31

28Y042-7F11-1 HEAVY CHAIN FRAGMENT

GLEWLGVIWASGGTDYNSALMSR
SEQ ID NO: 32

28Y042-7F11-1 HEAVY CHAIN FRAGMENT

NQVVLTMTNMDPVDTATYYCAR
SEQ ID NO: 33

28Y042-7F11-1 LIGHT CHAIN FRAGMENT

SGTASVVCLLNNFYPR
SEQ ID NO: 34

28Y042-7F11-1 LIGHT CHAIN FRAGMENT

VDNALQSGNSQESVTEQDSK
SEQ ID NO: 35

28Y042-7F11-1 LIGHT CHAIN FRAGMENT

SFNR
SEQ ID NO: 36

28Y042-7F11-1 LIGHT CHAIN FRAGMENT

ATINCK
SEQ ID NO: 37

28Y042-7F11-1 LIGHT CHAIN FRAGMENT

SSQSLLNSGNQK
SEQ ID NO: 38

28Y042-7F11-1 LIGHT CHAIN FRAGMENT

NYLAWYQQKPGQPPK
SEQ ID NO: 39

The present invention now being fully described, it will be apparent to one of ordinary skill in the art that many changes and modifications can be made thereto without departing from the spirit or scope of the appended claims.

The material in the ASCII text file named "PU66578P2_US_SeqList" created on Apr. 2, 2019, and having a size of 36,322 bytes is incorporated herein by reference in its entirety.

What is claimed is:

1. A composition comprising,
   a. a first antibody comprising a heavy chain amino acid sequence as shown in SEQ ID NO: 1 and a light chain amino acid sequence as shown in SEQ ID NO: 2; and
   b. a first variant form of the first antibody comprising a heavy chain amino acid sequence as shown in SEQ ID NO: 1 and a light chain amino acid sequence as shown in SEQ ID NO: 2, wherein position 60 of SEQ ID NO: 1 is N or S, position 317 of SEQ ID NO: 1 is N or S, and position 363 of SEQ ID NO: 1 is N or S.

2. The composition of claim 1, further comprising a second variant form of the first antibody, wherein the second variant form comprises a heavy chain amino acid sequence as shown in SEQ ID NO: 1 and a light chain amino acid sequence as shown in SEQ ID NO: 2, wherein position 22 of SEQ ID NO: 2 is N or S, position 37 of SEQ ID NO: 2 is N or S, and position 216 of SEQ ID NO: 2 is N or S.

3. The composition of claim 2, further comprising a third variant form of the first antibody, wherein the third variant form comprises a heavy chain amino acid sequence as shown in SEQ ID NO: 1 and a light chain amino acid sequence as shown in SEQ ID NO: 2, wherein position 60 of SEQ ID NO: 1 is N or S, position 317 of SEQ ID NO: 1 is N or S, position 363 of SEQ ID NO: 1 is N or S, position 22 of SEQ ID NO: 2 is N or S, position 37 of SEQ ID NO: 2 is N or S and position 216 of SEQ ID NO: 2 is N or S.

4. The composition of claim 2, wherein the second variant form of the first antibody comprises a heavy chain amino acid sequence as shown in SEQ ID NO: 1 and a light chain amino acid sequence as shown in SEQ ID NO: 2, wherein position 31 of SEQ ID NO: 2 is N or S, position 34 of SEQ ID NO: 2 is N or S, position 143 of SEQ ID NO: 2 is N or S, position 144 of SEQ ID NO: 2 is N or S, position 158 of SEQ ID NO: 2 is N or S, and position 164 of SEQ ID NO: 2 is N or S.

5. The composition of claim 4, wherein the first variant form of the first antibody comprises a heavy chain amino acid sequence as shown in SEQ ID NO: 1 and a light chain amino acid sequence as shown in SEQ ID NO: 2, wherein position 76 of SEQ ID NO: 1 is N or S, position 84 of SEQ ID NO: 1 is N or S, position 161 of SEQ ID NO: 1 is N or S, position 203 of SEQ ID NO: 1 is N or S, position 205 of SEQ ID NO: 1 is N or S, position 210 of SEQ ID NO: 1 is N or S, position 278 of SEQ ID NO: 1 is N or S, position 288 of SEQ ID NO: 1 is N or S, position 386 of SEQ ID NO: 1 is N or S, position 391 of SEQ ID NO: 1 is N or S, position 392 of SEQ ID NO: 1 is N or S, position 423 of SEQ ID NO: 1 is N or S and position 436 of SEQ ID NO: 1 is N or S.

6. The composition of claim 1, further comprising a third variant form of the first antibody, wherein the third variant form comprises a heavy chain amino acid sequence as shown in SEQ ID NO: 1 and a light chain amino acid sequence as shown in SEQ ID NO: 2, wherein position 60 of SEQ ID NO: 1 is N or S, position 317 of SEQ ID NO: 1 is N or S position 363 of SEQ ID NO: 1 is N or S, position 22 of SEQ ID NO: 2 is N or S, position 37 of SEQ ID NO: 2 is N or S and position 216 of SEQ ID NO: 2 Ss.

7. The composition of claim 6, wherein the third variant form of the first antibody comprises a heavy chain amino acid sequence as shown in SEQ ID NO: 1 and a light chain amino acid sequence as shown in SEQ ID NO: 2, wherein position 76 of SEQ ID NO: 1 is N or S, position 84 of SEQ ID NO: 1 is N or S, position 161 of SEQ ID NO: 1 is N or S, position 203 of SEQ ID NO: 1 is N or S, position 205 of SEQ ID NO: 1 is N or S, position 210 of SEQ ID NO: 1 is N or S, position 278 of SEQ ID NO: 1 is N or S, position 288 of SEQ ID NO: 1 is N or S, position 386 of SEQ ID NO: 1 is N or S, position 391 of SEQ ID NO: 1 is N or S, position 392 of SEQ ID NO: 1 is N or S, position 423 of SEQ ID NO: 1 is N or S, position 436 of SEQ ID NO: 1 is N or S, position 31 of SEQ ID NO: 2 is N or S, position 34 of SEQ ID NO: 2 is N or S, position 143 of SEQ ID NO: 2 is N or S, position 144 of SEQ ID NO: 2 is N or S, position 158 of SEQ ID NO: 2 is N or S, and position 164 of SEQ ID NO: 2 is N or S.

8. The composition of claim 1, wherein the first variant form of the first antibody comprises a heavy chain amino acid sequence as shown in SEQ ID NO: 1 and a light chain amino acid sequence as shown in SEQ ID NO: 2, wherein position 76 of SEQ ID NO: 1 is N or S, position 84 of SEQ ID NO: 1 is N or S, position 161 of SEQ ID NO: 1 is N or S, position 203 of SEQ ID NO: 1 is N or S, position 205 of SEQ ID NO: 1 is N or S, position 210 of SEQ ID NO: 1 is N or S, position 278 of SEQ ID NO: 1 is N or S, position 288 of SEQ ID NO: 1 is N or S, position 386 of SEQ ID NO: 1 is N or S, position 391 of SEQ ID NO: 1, position 392 of SEQ ID NO: 1 is N or S, position 423 of SEQ ID NO: 1 is N or S, and position 436 of SEQ ID NO: 1 is N or S.

9. A pharmaceutical composition comprising a pharmaceutically acceptable carrier and the composition of claim 1.

10. A composition comprising,
a. a first antibody comprising a heavy chain amino acid sequence as shown in SEQ ID NO: 1 and a light chain amino acid sequence as shown in SEQ ID NO: 2; and
b. a first variant form of the first antibody comprising a heavy chain amino acid sequence as shown in SEQ ID NO: 1 and a light chain amino acid sequence as shown in SEQ ID NO: 2, wherein position 22 of SEQ ID NO: 2 is N or S, position 37 of SEQ ID NO: 2 is N or S, and position 216 of SEQ ID NO: 2 is N or S.

11. The composition of claim 10, wherein the first variant form of the first antibody further comprises position 31 of SEQ ID NO: 2 is N or S, position 34 of SEQ ID NO: 2 is N or S, position 143 of SEQ ID NO: 2 is N or S, position 144 of SEQ ID NO: 2 is N or S, position 158 of SEQ ID NO: 2 is N or S, and position 164 of SEQ ID NO: 2 is N or S.

12. The composition of claim 10, further comprising a third variant form of the first antibody, wherein the third variant comprises a heavy chain amino acid sequence as shown in SEQ ID NO: 1 and a light chain amino acid sequence as shown in SEQ ID NO: 2, wherein comprising position 60 of SEQ ID NO: 1 is N or S, position 317 of SEQ ID NO: 1 is N or S position 363 of SEQ ID NO: 1 is N or S, position 22 of SEQ ID NO: 2 is N or S, position 37 of SEQ ID NO: 2 is N or S, and position 216 of SEQ ID NO: 2 is N or S.

13. The composition of claim 12, wherein the third variant form of the first antibody further comprises position 76 of SEQ ID NO: 1 is N or S, position 84 of SEQ ID NO: 1 is N or S, position 161 of SEQ ID NO: 1 is N or S, position 203 of SEQ ID NO: 1 is N or S, position 205 of SEQ ID NO: 1 is N or S, position 210 of SEQ ID NO: 1 is N or S, position 278 of SEQ ID NO: 1 is N or S, position 288 of SEQ ID NO: 1 is N or S, position 386 of SEQ ID NO: 1 is N or S, position 391 of SEQ ID NO: 1 is N or S, position 392 of SEQ ID NO: 1 is N or S, position 423 of SEQ ID NO: 1 is N or S, position 436 of SEQ ID NO: 1 is N or S, position 31 of SEQ ID NO: 2 is N or S, position 34 of SEQ ID NO: 2 is N or S, position 143 of SEQ ID NO: 2 is N or S, position 144 of SEQ ID NO: 2 is N or S, position 158 of SEQ ID NO: 2 is N or S and position 164 of SEQ ID NO: 2 is N or S.

14. A pharmaceutical composition comprising a pharmaceutically acceptable carrier and the composition of claim 10.

15. A composition comprising,
a. a first antibody comprising a heavy chain amino acid sequence as shown in SEQ ID NO: 1 and a light chain amino acid sequence as shown in SEQ ID NO: 2; and
b. a first variant form of the first antibody comprising a heavy chain amino acid sequence as shown in SEQ ID NO: 1 and a light chain amino acid sequence as shown in SEQ ID NO: 2, wherein position 60 of SEQ ID NO: 1 is N or S, position 317 of SEQ ID NO: 1 is N or S, position 363 of SEQ ID NO: 1 is N or S, position 22 of SEQ ID NO: 2 is N or S, position 37 of SEQ ID NO: 2 is N or S, and position 216 of SEQ ID NO: 2 is N or S.

16. The composition of claim 15, wherein the first variant form of the first antibody further comprises position 76 of SEQ ID NO: 1 is N or S, position 84 of SEQ ID NO: 1 is N or S, position 161 of SEQ ID NO: 1 is N or S, position 203 of SEQ ID NO: 1 is N or S, position 205 of SEQ ID NO: 1 is N or S, position 210 of SEQ ID NO: 1 is N or S, position 278 of SEQ ID NO: 1 is N or S, position 288 of SEQ ID NO: 1 is N or S, position 386 of SEQ ID NO: 1 is N or S, position 391 of SEQ ID NO: 1 is N or S, position 392 of SEQ ID NO: 1 is N or S, position 423 of SEQ ID NO: 1 is N or S, and position 436 of SEQ ID NO: 1 is N or S.

17. The composition of claim 16, wherein the first variant form of the first antibody further comprises position 31 of SEQ ID NO: 2 is N or S, position 34 of SEQ ID NO: 2 is N or S, position 143 of SEQ ID NO: 2 is N or S, position 144 of SEQ ID NO: 2 is N or S, position 158 of SEQ ID NO: 2 is N or S and position 164 of SEQ ID NO: 2 is N or S.

18. The composition of claim 15, wherein the first variant form of the first antibody further comprises position 31 of SEQ ID NO: 2 is N or S, position 34 of SEQ ID NO: 2 is N or S, position 143 of SEQ ID NO: 2 is N or S, position 144 of SEQ ID NO: 2 is N or S, position 158 of SEQ ID NO: 2 is N or S, and position 164 of SEQ ID NO: 2 is N or S.

19. A pharmaceutical composition comprising a pharmaceutically acceptable carrier and the composition of claim 15.

* * * * *

SEQUENCE LISTING

```
<160> NUMBER OF SEQ ID NOS: 39

<210> SEQ ID NO 1
<211> LENGTH: 449
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Gln Val Thr Leu Arg Glu Ser Gly Pro Ala Leu Val Lys Pro Thr Gln
```

-continued

```
1               5                   10                  15
Thr Leu Thr Leu Thr Cys Thr Val Ser Gly Phe Ser Leu Thr Gly Ser
                20                  25                  30

Ser Val His Trp Val Arg Gln Pro Gly Lys Gly Leu Glu Trp Leu
            35                  40                  45

Gly Val Ile Trp Ala Ser Gly Thr Asp Tyr Asn Ser Ala Leu Met
        50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Gly Leu Leu Arg Leu Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
        435                 440                 445

Lys

<210> SEQ ID NO 2
<211> LENGTH: 220
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 3
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Gly Ser
            20                  25                  30

Ser Val His Trp Val Arg Gln Pro Pro Gly Lys Gly Leu Glu Trp Leu
        35                  40                  45
```

```
Gly Val Ile Trp Ala Ser Gly Gly Thr Asp Tyr Asn Ser Ala Leu Met
        50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Gly Leu Leu Arg Leu Asp Tyr Trp Gly Arg Gly
                100                 105                 110

Thr Leu Val Thr Val Ser Ser
        115

<210> SEQ ID NO 4
<211> LENGTH: 114
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
                100                 105                 110

Lys Arg

<210> SEQ ID NO 5
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 5

Gly Ser Ser Val His
1               5

<210> SEQ ID NO 6
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

Val Ile Trp Ala Ser Gly Gly Thr Asp Tyr Asn Ser Ala Leu Met Ser
1               5                   10                  15

<210> SEQ ID NO 7
```

-continued

```
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 7

Asp Pro Pro Ser Gly Leu Leu Arg Leu Asp Tyr
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 8

Lys Ser Ser Gln Ser Leu Leu Asn Ser Gly Asn Gln Lys Asn Tyr Leu
1               5                   10                  15

Ala

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

Gly Ala Ser Thr Arg Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Gln Asn Val His Ser Phe Pro Phe Thr
1               5

<210> SEQ ID NO 11
<211> LENGTH: 115
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 11

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60
```

```
Val Glu Arg Leu Phe Lys Asn Leu Ser Leu Ile Lys Lys Tyr Ile Asp
 65                  70                  75                  80

Gly Gln Lys Lys Cys Gly Glu Arg Arg Val Asn Gln Phe
                 85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 12
<211> LENGTH: 400
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 12

Asp Leu Leu Pro Asp Glu Lys Ile Ser Leu Pro Pro Val Asn Phe
  1               5                  10                  15

Thr Ile Lys Val Thr Gly Leu Ala Gln Val Leu Leu Gln Trp Lys Pro
             20                  25                  30

Asn Pro Asp Gln Glu Gln Arg Asn Val Asn Leu Glu Tyr Gln Val Lys
         35                  40                  45

Ile Asn Ala Pro Lys Glu Asp Asp Tyr Glu Thr Arg Ile Thr Glu Ser
 50                  55                  60

Lys Cys Val Thr Ile Leu His Lys Gly Phe Ser Ala Ser Val Arg Thr
 65                  70                  75                  80

Ile Leu Gln Asn Asp His Ser Leu Leu Ala Ser Ser Trp Ala Ser Ala
                 85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
            115                 120                 125

Tyr Gln Val Ser Leu His Cys Thr Trp Leu Val Gly Thr Asp Ala Pro
130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
            195                 200                 205

Gln Leu Phe Ala Leu His Ala Ile Asp Gln Ile Asn Pro Pro Leu Asn
        210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
        275                 280                 285

Arg Ala Ala Val Ser Ser Met Cys Arg Glu Ala Gly Leu Trp Ser Glu
290                 295                 300
```

Trp Ser Gln Pro Ile Tyr Val Gly Asn Asp Glu His Lys Pro Leu Arg
305                 310                 315                 320

Glu Trp Phe Val Ile Val Ile Met Ala Thr Ile Cys Phe Ile Leu Leu
            325                 330                 335

Ile Leu Ser Leu Ile Cys Lys Ile Cys His Leu Trp Ile Lys Leu Phe
            340                 345                 350

Pro Pro Ile Pro Ala Pro Lys Ser Asn Ile Lys Asp Leu Phe Val Thr
            355                 360                 365

Thr Asn Tyr Glu Lys Ala Gly Ser Ser Glu Thr Glu Ile Glu Val Ile
            370                 375                 380

Cys Tyr Ile Glu Lys Pro Gly Val Glu Thr Leu Glu Asp Ser Val Phe
385                 390                 395                 400

<210> SEQ ID NO 13
<211> LENGTH: 1404
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 13
atgggctggt cctgcatcat cctgtttctg gtggccaccg ccaccggtgt gcacagccag      60
gtgaccctga gggagagcgg ccccgccctg gtgaagccca cagaccctc actctgacc      120
tgcaccgtga gcggcttcag cctgaccggc tctagcgtcc actgggtgag cagccccc      180
ggcaagggcc tggagtggct gggcgtgatc tgggcaagcg gggggacgga ctacaactcg      240
gccctgatga gcaggctctc catcagcaag gacaccagcc ggaaccaggt ggtgctgacc      300
atgaccaaca tggaccccgt ggacaccgcc acctattact gcgccaggga ccctccctcc      360
ggcctgctga ggctggacta ctggggcagg ggaacactag tgaccgtgtc cagcgccagc      420
accaagggcc ccagcgtgtt cccccctggcc ccagcagca agagcaccag cggcggcaca      480
gccgccctgg gctgcctggt gaaggactac ttccccgagc ccgtgaccgt gtcctggaac      540
agcggagccc tgaccagcgg cgtgcacacc ttccccgccg tgctgcagag cagcggcctg      600
tacagcctga gcagcgtggt gaccgtgccc agcagcagcc tgggcacca gacctacatc      660
tgtaacgtga accacaagcc cagcaacacc aaggtggaca gcgggtgga gcccaagagc      720
tgtgacaaga cccacacctg ccccccctgc cctgcccccg agctgctggg aggccccagc      780
gtgttcctgt tcccccccaa gcctaaggac accctgtaca tcaccagaga cccgaggtg      840
acctgtgtgg tggtggatgt gagccacgag gaccctgagg tgaagttcaa ctggtacgtg      900
gacggcgtgg aggtgcacaa tgccaagacc aagcccaggg aggagcagta caacagcacc      960
taccggtgg tgtccgtgct gaccgtgctg caccaggatt ggctgaacgg caaggagtac      1020
aagtgtaagg tgtccaacaa ggcccctgcct gcccctatcg agaaaaccat cagcaaggcc      1080
aagggccagc ccagagagcc ccaggtgtac accctgcccc ctagcagaga ggagatgacc      1140
aagaaccagg tgtccctgac ctgcctggtg aagggcttct accccagcga catcgccgtg      1200
gagtgggaga gcaacggcca gcccgagaac aactacaaga ccacccccc tgtgctggac      1260
agcgatggca gcttcttcct gtacagcaag ctgaccgtgg acaagagcag atggcagcag      1320
ggcaacgtgt tcagctgctc cgtgatgcac gaggccctgc acaatcacta cacccagaag      1380
agcctgagcc tgtcccctgg caag                                            1404

```
<210> SEQ ID NO 14
<211> LENGTH: 717
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 14
atgggctggt cctgcatcat cctgtttctg gtggccaccg ccaccggtgt gcacagcgac      60
atcgtgatga cccagtctcc cgattcactg gccgtgagcc tgggcgagag ggccaccatc     120
aactgcaaga gcagccagag cctcctgaac agcggcaacc agaagaacta cctggcctgg     180
taccagcaga aacccggcca gccccccaag ctgctgatct atggcgcctc caccagggag     240
agcggcgtgc cagacaggtt tagcggcagc ggcagcggca ccgacttcac cctgacaatc     300
agcagcctgc aggccgagga cgtggccgtg tactactgcc agaacgtcca gcttcccc      360 ttcaccttcg gcgggggaac caagctggag atcaagcgta cggtggccgc ccccagcgtg     420
ttcatcttcc cccccagcga tgagcagctg aagagcggca ccgccagcgt ggtgtgtctg     480
ctgaacaact ctacccccg ggaggccaag gtgcagtgga aggtggacaa tgccctgcag     540
agcggcaaca gccaggagag cgtgaccgag caggacagca aggactccac ctacagcctg     600
agcagcaccc tgaccctgag caaggccgac tacgagaagc acaaggtgta cgcctgtgag     660
gtgacccacc agggcctgtc cagccccgtg accaagagct caaccgggg cgagtgc        717

<210> SEQ ID NO 15
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 15
caggtgaccc tgagggagag cggccccgcc ctggtgaagc ccacacagac cctcactctg      60
acctgcaccg tgagcggctt cagcctgacc ggctctagcg tccactgggt gaggcagccc     120
cccggcaagg gcctggagtg gctgggcgtg atctgggcaa gcgggggac ggactacaac     180 tcggccctga tgagcaggct ctccatcagc aaggacacca gcggaacca ggtggtgctg     240 accatgacca catggaccc cgtggacacc gccacctatt actgcgccag ggaccctccc     300
tccggcctgc tgaggctgga ctactggggc aggggaacac tagtgaccgt gtccagc        357

<210> SEQ ID NO 16
<211> LENGTH: 342
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 16
gacatcgtga tgacccagtc tcccgattca ctggccgtga gcctgggcga gagggccacc      60
atcaactgca gagcagcca gagcctcctg aacagcggca accagaagaa ctacctggcc     120
tggtaccagc agaaacccgg ccagcccccc aagctgctga tctatggcgc ctccaccagg     180
gagagcggcg tgccagacag gtttagcggc agcggcagcg gcaccgactt caccctgaca     240
atcagcagcc tgcaggccga ggacgtggcc gtgtactact gccagaacgt ccacagcttc     300
cccttcacct tcggcggggg aaccaagctg gagatcaagc gt                         342
```

<210> SEQ ID NO 17
<211> LENGTH: 1347
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 17

```
caggtgaccc tgagggagag cggccccgcc ctggtgaagc ccacacagac cctcactctg      60
acctgcaccg tgagcggctt cagcctgacc ggctctagcg tccactgggt gaggcagccc     120
cccggcaagg gcctggagtg gctgggcgtg atctgggcaa gcggggggac ggactacaac     180
tcggccctga tgagcaggct ctccatcagc aaggacacca gccggaacca ggtggtgctg     240
accatgacca acatggaccc cgtggacacc gccacctatt actgcgccag ggaccctccc     300
tccggcctgc tgaggctgga ctactggggc aggggaacac tagtgaccgt gtccagcgcc     360
agcaccaagg gcccagcgt gttccccctg gcccccagca gcaagagcac cagcggcggc     420
acagccgccc tgggctgcct ggtgaaggac tacttccccg agcccgtgac cgtgtcctgg     480
aacagcggag ccctgaccag cggcgtgcac accttccccg ccgtgctgca gagcagcggc     540
ctgtacagcc tgagcagcgt ggtgaccgtg cccagcagca gcctgggcac ccagacctac     600
atctgtaacg tgaaccacaa gcccagcaac accaaggtgg acaagcgggt ggagcccaag     660
agctgtgaca agacccacac ctgcccccccc tgccctgccc ccgagctgct gggaggcccc     720
agcgtgttcc tgttcccccc caagcctaag gacaccctgt acatcaccag agaacccgag     780
gtgacctgtg tggtggtgga tgtgagccac gaggaccctg aggtgaagtt caactggtac     840
gtggacggcg tggaggtgca caatgccaag accaagccca gggaggagca gtacaacagc     900
acctaccggg tggtgtccgt gctgaccgtg ctgcaccagg attggctgaa cggcaaggag     960
tacaagtgta aggtgtccaa caaggccctg cctgccccta tcgagaaaac catcagcaag    1020
gccaagggcc agcccagaga gccccaggtg tacaccctgc ccctagcag agaggagatg    1080 accaagaacc aggtgtccct gacctgcctg gtgaagggct tctacccag cgacatcgcc    1140 gtggagtggg agagcaacgg ccagcccgag aacaactaca agaccacccc cctgtgctg    1200 gacagcgatg gcagcttctt cctgtacagc aagctgaccg tggacaagag cagatggcag    1260
cagggcaacg tgttcagctg ctccgtgatg cacgaggccc tgcacaatca ctacacccag    1320
aagagcctga gcctgtcccc tggcaag                                        1347
```

<210> SEQ ID NO 18
<211> LENGTH: 660
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 18

```
gacatcgtga tgacccagtc tcccgattca ctggccgtga gcctgggcga gagggccacc      60
atcaactgca gagcagcca gagcctcctg aacagcggca accagaagaa ctacctggcc     120
tggtaccagc agaaacccgg ccagccccccc aagctgctga tctatggcgc ctccaccagg     180
gagagcggcg tgccagacag gtttagcggc agcggcagcg gcaccgactt caccctgaca     240
atcagcagcc tgcaggccga ggacgtggcc gtgtactact gccagaacgt ccacagcttc     300
```

-continued

```
cccttcacct tcggcggggg aaccaagctg gagatcaagc gtacggtggc cgcccccagc    360
gtgttcatct tccccccag cgatgagcag ctgaagagcg gcaccgccag cgtggtgtgt    420
ctgctgaaca acttctaccc ccgggaggcc aaggtgcagt ggaaggtgga caatgccctg    480
cagagcggca acagccagga gagcgtgacc gagcaggaca gcaaggactc cacctacagc    540
ctgagcagca ccctgaccct gagcaaggcc gactacgaga agcacaaggt gtacgcctgt    600
gaggtgaccc accagggcct gtccagcccc gtgaccaaga gcttcaaccg ggcgagtgc     660
```

<210> SEQ ID NO 19
<211> LENGTH: 19
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 19

Met Gly Trp Ser Cys Ile Ile Leu Phe Leu Val Ala Thr Ala Thr Gly
1               5                   10                  15

Val His Ser

<210> SEQ ID NO 20
<211> LENGTH: 19
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 20

Met Gly Trp Ser Cys Ile Ile Leu Phe Leu Val Ala Thr Ala Thr Gly
1               5                   10                  15

Val His Ser

<210> SEQ ID NO 21
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 21

Trp Gly Arg Gly Thr Leu Val Thr Val Ser Ser
1               5                   10

<210> SEQ ID NO 22
<211> LENGTH: 449
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 60, 76, 84, 161, 203, 205, 210, 278, 288, 317, 363, 386,
      391, 392, 423, 436
<223> OTHER INFORMATION: Xaa = Any Amino Acid

<400> SEQUENCE: 22

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Gly Ser
                20                  25                  30

Ser Val His Trp Val Arg Gln Pro Pro Gly Lys Gly Leu Glu Trp Leu
         35                  40                  45

Gly Val Ile Trp Ala Ser Gly Gly Thr Asp Tyr Xaa Ser Ala Leu Met
 50                  55                  60

Ser Arg Leu Ser Ile Ser Lys Asp Thr Ser Arg Xaa Gln Val Val Leu
 65                  70                  75                  80

Thr Met Thr Xaa Met Asp Pro Val Asp Thr Ala Thr Tyr Tyr Cys Ala
             85                  90                  95

Arg Asp Pro Pro Ser Gly Leu Leu Arg Leu Asp Tyr Trp Gly Arg Gly
             100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
             130                 135                 140

Gly Cys Leu Val Lys Asp Tyr Phe Pro Glu Pro Val Thr Val Ser Trp
145                 150                 155                 160

Xaa Ser Gly Ala Leu Thr Ser Gly Val His Thr Phe Pro Ala Val Leu
             165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Xaa Val Xaa His Lys Pro
             195                 200                 205

Ser Xaa Thr Lys Val Asp Lys Arg Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Thr
             245                 250                 255

Arg Glu Pro Glu Val Thr Cys Val Val Val Asp Val Ser His Glu Asp
             260                 265                 270

Pro Glu Val Lys Phe Xaa Trp Tyr Val Asp Gly Val Glu Val His Xaa
             275                 280                 285

Ala Lys Thr Lys Pro Arg Glu Glu Gln Tyr Asn Ser Thr Tyr Arg Val
             290                 295                 300

Val Ser Val Leu Thr Val Leu His Gln Asp Trp Leu Xaa Gly Lys Glu
305                 310                 315                 320

Tyr Lys Cys Lys Val Ser Asn Lys Ala Leu Pro Ala Pro Ile Glu Lys
             325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Xaa Gln Val Ser Leu Thr
             355                 360                 365

Cys Leu Val Lys Gly Phe Tyr Pro Ser Asp Ile Ala Val Glu Trp Glu
370                 375                 380

Ser Xaa Gly Gln Pro Glu Xaa Xaa Tyr Lys Thr Thr Pro Pro Val Leu
385                 390                 395                 400

Asp Ser Asp Gly Ser Phe Phe Leu Tyr Ser Lys Leu Thr Val Asp Lys
             405                 410                 415

Ser Arg Trp Gln Gln Gly Xaa Val Phe Ser Cys Ser Val Met His Glu
             420                 425                 430

Ala Leu His Xaa His Tyr Thr Gln Lys Ser Leu Ser Leu Ser Pro Gly
             435                 440                 445

Lys

<210> SEQ ID NO 23
<211> LENGTH: 220
<212> TYPE: PRT
<213> ORGANISM: Artificial Sequence
<220> FEATURE:
<223> OTHER INFORMATION: Amino acid sequence identified using molecular biology techniques.
<220> FEATURE:
<221> NAME/KEY: VARIANT
<222> LOCATION: 22, 31, 34, 37, 143, 144, 158, 164, 216
<223> OTHER INFORMATION: Xaa = Any Amino Acid

<400> SEQUENCE: 23

Asp Ile Val Met Thr Gln Ser Pro Asp Ser Leu Ala Val Ser Leu Gly
1               5                   10                  15

Glu Arg Ala Thr Ile Xaa Cys Lys Ser Ser Gln Ser Leu Leu Xaa Ser
            20                  25                  30

Gly Xaa Gln Lys Xaa Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Xaa Xaa
    130                 135                 140

Phe Tyr Pro Arg Glu Ala Lys Val Gln Trp Lys Val Asp Xaa Ala Leu
145                 150                 155                 160

Gln Ser Gly Xaa Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Xaa Arg Gly Glu Cys
    210                 215                 220

<210> SEQ ID NO 24
<211> LENGTH: 1347
<212> TYPE: DNA
<213> ORGANISM: Artificial Sequence
<220> FEATURE:
<223> OTHER INFORMATION: Nucleic acid sequence identified using molecular biology techniques.
<220> FEATURE:
<221> NAME/KEY: misc_feature
<222> LOCATION: 178, 179, 180, 226, 227, 228, 250, 251, 252, 481, 482, 483, 607, 608, 609, 613, 614, 615, 628, 629, 630, 832, 833, 834, 862, 863, 864, 949, 950, 951, 1087, 1088, 1089, 1156, 1157, 1158, 1171, 1172, 1173, 1174, 1175, 1176, 1267, 1268
<223> OTHER INFORMATION: n = A,T,C or G
<220> FEATURE:
<221> NAME/KEY: misc_feature
<222> LOCATION: 1269, 1306, 1307, 1308
<223> OTHER INFORMATION: n = A,T,C or G

<400> SEQUENCE: 24

```
caggtgaccc tgagggagag cggcccgcc ctggtgaagc ccacacagac cctcactctg      60
acctgcaccg tgagcggctt cagcctgacc ggctctagcg tccactgggt gaggcagccc    120
cccggcaagg gcctggagtg gctgggcgtg atctgggcaa gcggggggac ggactacnnn    180
tcggccctga tgagcaggct ctccatcagc aaggacacca gccggnnnca ggtggtgctg    240
accatgaccn nnatggaccc cgtggacacc gccacctatt actgcgccag ggaccctccc    300
tccggcctgc tgaggctgga ctactggggc aggggaacac tagtgaccgt gtccagcgcc    360
agcaccaagg gcccagcgt gttccccctg gccccagca gcaagagcac cagcggcggc      420
acagccgccc tgggctgcct ggtgaaggac tacttccccg agcccgtgac cgtgtcctgg    480
nnnagcggag ccctgaccag cggcgtgcac accttccccg ccgtgctgca gagcagcggc    540
ctgtacagcc tgagcagcgt ggtgaccgtg cccagcagca gcctgggcac ccagacctac    600
atctgtnnng tgnnncacaa gcccagcnnn accaaggtgg acaagcgggt ggagcccaag    660
agctgtgaca agacccacac ctgccccccc tgccctgccc ccgagctgct gggaggcccc    720
agcgtgttcc tgttcccccc caagcctaag gacaccctgt acatcaccag agaacccgag    780
gtgacctgtg tggtggtgga tgtgagccac gaggaccctg aggtgaagtt cnnntggtac    840
gtggacggcg tggaggtgca cnnngccaag accaagccca gggaggagca gtacaacagc    900
acctaccggg tggtgtccgt gctgaccgtg ctgcaccagg attggctgnn nggcaaggag    960
tacaagtgta aggtgtccaa caaggccctg cctgcccta tcgagaaaac catcagcaag    1020
gccaagggcc agcccagaga gccccaggtg tacaccctgc cccctagcag agaggagatg   1080
accaagnnnc aggtgtccct gacctgcctg gtgaagggct tctaccccag cgacatcgcc   1140
gtggagtggg agagcnnngg ccagcccgag nnnnnntaca agaccacccc ccctgtgctg   1200
gacagcgatg gcagcttctt cctgtacagc aagctgaccg tggacaagag cagatggcag   1260
cagggcnnng tgttcagctg ctccgtgatg cacgaggccc tgcacnnnca ctacacccag   1320
aagagcctga gcctgtcccc tggcaag                                      1347
```

<210> SEQ ID NO 25
<211> LENGTH: 660
<212> TYPE: DNA
<213> ORGANISM: Artificial Sequence
<220> FEATURE:
<223> OTHER INFORMATION: Nucleic acid sequence identified using
 molecular biology techniques.
<220> FEATURE:
<221> NAME/KEY: misc_feature
<222> LOCATION: 64, 65, 66, 91, 92, 93, 100, 101, 102, 109, 110, 111,
 427, 428, 429, 430, 431, 432, 472, 473, 474, 490, 491, 492, 646,
 647, 648
<223> OTHER INFORMATION: n = A,T,C or G

<400> SEQUENCE: 25

```
gacatcgtga tgacccagtc tcccgattca ctggccgtga gcctgggcga gagggccacc      60
atcnnntgca agagcagcca gagcctcctg nnnagcggcn nncagaagnn ntacctggcc    120
tggtaccagc agaaacccgg ccagcccccc aagctgctga tctatggcgc ctccaccagg    180
gagagcggcg tgccagacag gtttagcggc agcggcagcg gcaccgactt caccctgaca    240
atcagcagcc tgcaggccga ggacgtggcc gtgtactact gccagaacgt ccacagcttc    300
ccccttcacct tcggcggggg aaccaagctg gagatcaagc gtacggtggc cgcccccagc    360
gtgttcatct tcccccccag cgatgagcag ctgaagagcg gcaccgccag cgtggtgtgt    420
```

```
ctgctgnnnn nnttctaccc ccgggaggcc aaggtgcagt ggaaggtgga cnnngccctg      480
cagagcggcn nnagccagga gagcgtgacc gagcaggaca gcaaggactc cacctacagc      540
ctgagcagca ccctgaccct gagcaaggcc gactacgaga agcacaaggt gtacgcctgt      600
gaggtgaccc ccagggcct gtccagcccc gtgaccaaga gcttcnnncg gggcgagtgc       660
```

```
<210> SEQ ID NO 26
<211> LENGTH: 63
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 26

Asp Tyr Phe Pro Glu Pro Val Thr Val Ser Trp Asn Ser Gly Ala Leu
1               5                   10                  15

Thr Ser Gly Val His Thr Phe Pro Ala Val Leu Gln Ser Ser Gly Leu
            20                  25                  30

Tyr Ser Leu Ser Ser Val Val Thr Val Pro Ser Ser Ser Leu Gly Thr
        35                  40                  45

Gln Thr Tyr Ile Cys Asn Val Asn His Lys Pro Ser Asn Thr Lys
    50                  55                  60

<210> SEQ ID NO 27
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 27

Phe Asn Trp Tyr Val Asp Gly Val Glu Val His Asn Ala Lys
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 28

Val Val Ser Val Leu Thr Val Leu His Gln Asp Trp Leu Asn Gly Lys
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 29

Asn Gln Val Ser Leu Thr Cys Leu Val Lys
1               5                   10

<210> SEQ ID NO 30
<211> LENGTH: 22
<212> TYPE: PRT
<213> ORGANISM: Artificial Sequence
<220> FEATURE:
```

<223> OTHER INFORMATION: Amino acid sequence identified using molecular
      biology techniques.

<400> SEQUENCE: 30

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 31
<211> LENGTH: 23
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 31

Trp Gln Gln Gly Asn Val Phe Ser Cys Ser Val Met His Glu Ala Leu
1               5                   10                  15

His Asn His Tyr Thr Gln Lys
            20

<210> SEQ ID NO 32
<211> LENGTH: 23
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 32

Gly Leu Glu Trp Leu Gly Val Ile Trp Ala Ser Gly Gly Thr Asp Tyr
1               5                   10                  15

Asn Ser Ala Leu Met Ser Arg
            20

<210> SEQ ID NO 33
<211> LENGTH: 23
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 33

Gly Leu Glu Trp Leu Gly Val Ile Trp Ala Ser Gly Gly Thr Asp Tyr
1               5                   10                  15

Asn Ser Ala Leu Met Ser Arg
            20

<210> SEQ ID NO 34
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 34

Ser Gly Thr Ala Ser Val Val Cys Leu Leu Asn Asn Phe Tyr Pro Arg
1               5                   10                  15

<210> SEQ ID NO 35
<211> LENGTH: 20

```
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 35

Val Asp Asn Ala Leu Gln Ser Gly Asn Ser Gln Glu Ser Val Thr Glu
1               5                   10                  15

Gln Asp Ser Lys
            20

<210> SEQ ID NO 36
<211> LENGTH: 4
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 36

Ser Phe Asn Arg
1

<210> SEQ ID NO 37
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 37

Ala Thr Ile Asn Cys Lys
1               5

<210> SEQ ID NO 38
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 38

Ser Ser Gln Ser Leu Leu Asn Ser Gly Asn Gln Lys
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 39

Asn Tyr Leu Ala Trp Tyr Gln Gln Lys Pro Gly Gln Pro Pro Lys
1               5                   10                  15
```